United States Patent
Mitchell et al.

(10) Patent No.: US 9,006,165 B2
(45) Date of Patent: Apr. 14, 2015

(54) LOW-VOC CLEANING SUBSTRATES AND COMPOSITIONS COMPRISING A CATIONIC BIOCIDE AND GLYCOL ETHER SOLVENT

(71) Applicant: The Clorox Company, Oakland, CA (US)

(72) Inventors: Diana Mitchell, Pleasanton, CA (US); Sarah Coulter, Pleasanton, CA (US); Ashish Kumar Jha, Pleasanton, CA (US); William Ouellette, Pleasanton, CA (US); Gregory VanBuskirk, Danville, CA (US)

(73) Assignee: The Clorox Company, Oakland, CA (US)

( * ) Notice: Subject to any disclaimer, the term of this patent is extended or adjusted under 35 U.S.C. 154(b) by 0 days.

(21) Appl. No.: 14/174,698

(22) Filed: Feb. 6, 2014

(65) Prior Publication Data

US 2014/0150193 A1    Jun. 5, 2014

Related U.S. Application Data

(63) Continuation of application No. 13/543,232, filed on Jul. 6, 2012, now Pat. No. 8,648,027.

(51) Int. Cl.
| | | |
|---|---|---|
| *C11D 1/835* | (2006.01) |
| *C11D 3/44* | (2006.01) |
| *C11D 3/48* | (2006.01) |
| *A47L 13/17* | (2006.01) |
| *C11D 3/43* | (2006.01) |
| *C11D 1/00* | (2006.01) |
| *C11D 1/62* | (2006.01) |
| *C11D 1/72* | (2006.01) |

(52) U.S. Cl.
CPC . *C11D 3/48* (2013.01); *A47L 13/17* (2013.01); *C11D 1/835* (2013.01); *C11D 3/43* (2013.01); *C11D 1/008* (2013.01); *C11D 1/62* (2013.01); *C11D 1/72* (2013.01)

(58) Field of Classification Search
USPC ......... 510/199, 238, 271, 295, 362, 365, 384, 510/391, 421, 432, 504
See application file for complete search history.

(56) References Cited

U.S. PATENT DOCUMENTS

| | | | |
|---|---|---|---|
| 2,684,924 A | 7/1954 | Swain et al. |
| 2,990,425 A | 6/1961 | Senior |
| 3,468,898 A | 9/1969 | Cutler et al. |
| 4,022,834 A | 5/1977 | Gunderson |
| 4,053,636 A | 10/1977 | Eustis, III et al. |
| 4,198,392 A | 4/1980 | Juneja |
| 4,463,045 A | 7/1984 | Ahr et al. |
| 4,540,505 A * | 9/1985 | Frazier | 510/384 |
| 5,145,604 A * | 9/1992 | Neumiller | 516/71 |
| 5,292,581 A | 3/1994 | Viazmensky et al. |
| 5,444,094 A | 8/1995 | Malik et al. |
| 5,454,984 A | 10/1995 | Graubart et al. |
| 5,522,942 A | 6/1996 | Graubart et al. |
| 5,798,329 A | 8/1998 | Taylor et al. |
| 5,814,591 A * | 9/1998 | Mills et al. | 510/238 |
| 5,908,854 A | 6/1999 | McCue et al. |
| 5,922,665 A | 7/1999 | Liu |
| 5,948,743 A * | 9/1999 | Fonsny et al. | 510/280 |
| 6,017,869 A * | 1/2000 | Lu et al. | 510/384 |
| 6,080,706 A * | 6/2000 | Blanvalet et al. | 510/108 |
| 6,090,768 A | 7/2000 | Delaney et al. |
| 6,110,295 A * | 8/2000 | Lu et al. | 134/42 |
| 6,121,224 A * | 9/2000 | Fonsny et al. | 510/384 |
| 6,130,197 A | 10/2000 | Bedford et al. |
| 6,143,244 A | 11/2000 | Xia et al. |
| 6,143,281 A | 11/2000 | Alexander et al. |
| 6,153,568 A | 11/2000 | McCanna et al. |
| 6,187,737 B1 | 2/2001 | Geke et al. |
| 6,277,805 B1 | 8/2001 | Kupneski |
| 6,323,171 B1 * | 11/2001 | Fonsny et al. | 510/384 |
| 6,339,057 B1 | 1/2002 | Knox et al. |
| 6,342,474 B1 | 1/2002 | Kerobo et al. |
| 6,358,900 B1 | 3/2002 | Wigley et al. |
| 6,376,455 B1 | 4/2002 | Friedli et al. |
| 6,387,855 B1 * | 5/2002 | De La Mettrie | 510/122 |
| 6,387,866 B1 | 5/2002 | Mondin et al. |
| 6,429,183 B1 * | 8/2002 | Leonard et al. | 510/438 |
| 6,462,014 B1 | 10/2002 | Johnson et al. |
| 6,583,104 B1 | 6/2003 | Christensen et al. |
| 6,693,070 B1 | 2/2004 | Cheung et al. |
| 6,844,308 B1 * | 1/2005 | Dastbaz et al. | 510/438 |
| 6,849,589 B2 | 2/2005 | Liu |
| 7,071,155 B2 | 7/2006 | Griese et al. |
| 7,214,651 B2 | 5/2007 | Mohr et al. |
| 7,348,303 B2 | 3/2008 | Gallotti et al. |
| 7,530,361 B2 | 5/2009 | Killeen et al. |

(Continued)

FOREIGN PATENT DOCUMENTS

| | | |
|---|---|---|
| CA | 2132274 A1 | 5/1995 |
| DE | 2212259 A1 | 10/1972 |

(Continued)

OTHER PUBLICATIONS

International Search Report, mailed Jul. 29, 2013, from counterpart PCT/US13/48586; Jun. 28, 2013.

*Primary Examiner* — Charles Boyer

(74) *Attorney, Agent, or Firm* — Erin Collins

(57) ABSTRACT

A cleaning composition for sanitizing and/or disinfecting hard surfaces, comprising:

a cationic biocide, surfactant and low levels of VOC solvents. The cleaning composition is adapted to clean a variety of hard surfaces without leaving behind a visible residue and creates low levels of streaking and filming on the treated surface. The cleaning composition contains less than 5% by weight of VOCs. The cleaning composition may be used alone as a liquid or spray formulation or in combination with a substrate, for example, a pre-loaded cleaning wipe.

20 Claims, 5 Drawing Sheets

(56) References Cited

U.S. PATENT DOCUMENTS

| | | |
|---|---|---|
| 2003/0073600 A1* | 4/2003 | Avery et al. .............. 510/382 |
| 2003/0228991 A1 | 12/2003 | Johnson et al. |
| 2004/0224867 A1* | 11/2004 | Colurciello et al. ......... 510/238 |
| 2005/0148655 A1* | 7/2005 | Manzer .............. 514/424 |
| 2005/0227898 A1 | 10/2005 | Leskowicz et al. |
| 2006/0016785 A1 | 1/2006 | Egbe et al. |
| 2006/0052264 A1 | 3/2006 | Lu |
| 2006/0172912 A1* | 8/2006 | Burt et al. ................ 510/383 |
| 2006/0234899 A1* | 10/2006 | Nekmard et al. ........... 510/439 |
| 2008/0261856 A1* | 10/2008 | Nakagawa et al. ......... 510/421 |
| 2008/0287331 A1 | 11/2008 | Lin et al. |
| 2010/0249245 A1 | 9/2010 | Whiteley et al. |
| 2010/0323895 A1 | 12/2010 | Garner |
| 2011/0098206 A1 | 4/2011 | Lynch et al. |
| 2011/0219312 A1* | 9/2011 | Kim et al. .................. 715/739 |
| 2011/0311600 A1* | 12/2011 | Polzin et al. ............... 424/409 |
| 2012/0034287 A1* | 2/2012 | Napolitano et al. ........ 424/409 |

FOREIGN PATENT DOCUMENTS

| | | |
|---|---|---|
| DE | 2627548 A1 | 1/1977 |
| DE | 1964196 B2 | 2/1977 |
| EP | 0024031 B2 | 5/1987 |
| WO | 2007073877 A1 | 7/2007 |
| WO | 2011064554 A1 | 6/2011 |

* cited by examiner

Low Cloud Point/ Uniform Micron-structure Residue Example

High Cloud Point/Irregular Residue Example

Residue Examples of Low VOC Composition at Different Cloud Point Levels
(top left CP= 85°F, top right CP =83°F, bottom left CP= 81°F, bottom right CP= 78°F)

LOW-VOC CLEANING SUBSTRATES AND COMPOSITIONS COMPRISING A CATIONIC BIOCIDE AND GLYCOL ETHER SOLVENT

CROSS-REFERENCES TO RELATED APPLICATIONS

This application is a continuation application and claims priority to co-pending U.S. application Ser. No. 13/543,232, filed on Jul. 6, 2012, which is hereby incorporated by reference.

The present invention relates to cleaning compositions that include a cationic biocide and has low levels of volatile organic compounds (VOCs). The cleaning composition can be used alone, in combination with one or more other cleaning compositions, and/or in combination wipe, towel, cloth, rag, sponge, mop, squeegee, and the like.

BACKGROUND OF THE INVENTION

Many types of cleaning compositions have been developed to clean various types of products and/or surfaces. Some of these cleaning compositions included one or more compounds to disinfect, sanitize, and/or sterilize the product and/or surface. The present invention relates to a cleaning composition that includes at least one cationic biocides such as, but not limited to, quaternary ammonium salts ("quats") as the anti-microbial active. The cleaning composition can include other traditional anti-microbial actives such as, but not limited to, one or more acids and/or alcohols. In addition, the cleaning composition also includes one or more surfactants and one or more solvents which together provide excellent cleaning efficacy with low levels of residue and little to no visible streaking and filming on the surface being treated. Other traditional cleaning compositions with good cleaning efficacy and low levels of visible residue contain higher levels of VOC solvents, for example between 1-40% by weight of the composition. The cleaning composition is envisioned as being used in a wide variety of applications. As can be appreciated, the additives, the surfactants, the solvents and the cationic biocides used in the cleaning compositions, may vary depending on the particular application of the cleaning composition.

One type of biocide that has been used in cleaning wipes is quaternary amines or "quats". Liquid cleaners applied to cleaning wipes typically include relatively large amounts of quat. These cleaning wipes are typically used on hard surfaces such as floors, countertops, glass surfaces, sinks, toilets, appliances, and/or the like. Although quats are excellent biocides, quats can cause skin irritation when used in too high of concentrations. In addition, not all of the quat may be released from the wipe when the wipe is applied to a surface, thus added quat is included in the liquid cleaner to ensure that the desired amount of quat transfers to the cleaned surface. Other biocides such as biguanide compounds also have a low release rate from the wipe. Since the quat and/or biguanide compound is typically one of the higher cost components of the cleaner, the larger quat and/or biguanide concentrations used in the liquid cleaner translates into higher product costs. There have been various attempts to develop liquid cleaners having improved quat release from the cleaning wipes. Some cleaning formulations use a high weight percentage of VOCs to promote quat release from the cleaning wipe. It has been observed that isopropyl alcohol in amounts of over about 12% can improve the quat release from the wipe. The use of isopropyl alcohol is also beneficial in that the alcohol has its own antimicrobial properties and cost substantially less than quats. Although the use of isopropyl alcohol in the cleaning formulation improves quat release from the wipe, a substantial amount of quat still remains on the cleaning wipe after use. In addition, local, state and/or federal governments have begun to promulgate regulations on the amount of VOCs can be used in cleaners. As a result, cleaners having high concentrations (e.g. greater than 0.5% by weight of the composition) of VOCs may be less preferred.

In addition, quats also tend to leave residues and/or cause streaking after being applied to various surfaces. The residue and streaking problems are of great concern to consumers since the visual appearance of the cleaned surface functions as an indicator of the effectiveness of the cleaner. Consumers also judge the cleaning effectiveness of the cleaner by touching the cleaned surface. Sticky surfaces typically indicate to the consumer that the surface has not been effectively cleaned. Cleaning formulations that tend to leave residues and/or cause streaking tend to produce a less shiny, thus a visually perceived less clean surface, and further tend to leave a sticky surface. This is especially true with mop and pre-loaded wipe applications, where such compositions are left to dry on the surface without rinsing. As a result, the consumer perceives that the cleaned surface has not been effectively cleaned irrespective of the fact the surface may have been properly cleaned and disinfected. Liquid cleaners having high quat content are also subject to various local, state and/or federal regulations due to the toxicity of the quat in high concentrations.

In view of the present state of the art of cleaning compositions, there is a demand for a low VOC formulation with excellent cleaning efficacy that can be used in a variety of applications to disinfect, sanitize, and/or sterilize surfaces without leaving undesired residues and/or streaking on the cleaned surface, and/or which cleaning composition is cost effective to use.

SUMMARY OF THE INVENTION

The present invention is related to a cleaning composition that includes a cationic biocide. The cleaning composition is generally a liquid cleaner or a liquid loaded onto a substrate; however, the cleaning composition may be in an aerosol, liquid spray or semi-solid form. The cleaning composition can be used by itself or combined with other cleaning formulations. The cleaning composition of the present invention has: excellent cleaning performance, low levels of streaking and filming and/or visible residue, and has low levels of VOCs, less than 5% by weight of the composition; or less than about 3% by weight; or even less than 2% by weight of the composition.

Typically high-VOC formulations are used for low streaking and filming cleaners because there is no phase separation as the formulation dries on a hard surface that is being cleaned. The present invention teaches that it is possible to have a low VOC cleaning formulation that has good filming/streaking performance even though the composition does phase separate upon drying on a treated surface. The low VOC cleaning formulation of the present invention creates a regular micron-structure and leaves a residue on the surface being treated/cleaned, but the residue forms a regular pattern of light and dark areas with a length scale below the visual threshold of what the human eye perceives. Therefore, although the cleaning composition of the present invention leaves a residue on the treated surface, the residue is substantially invisible to the human eye.

As the cleaning composition of the present invention dries on the surface, two processes occur: dewetting and phase separation. Dewetting is when the liquid film ruptures upon drying to form individual drops. Depending on the specific formulation, if the cloud point of the formulation is at 95° F. or less; or 90° F. or less, or even 85° F. or less then phase separation will occur before dewetting which allows for the cleaning composition to form a regular micron-scale structure and that leads to a residue that contains a regular pattern of small droplets. The regular pattern of small droplets is substantially invisible to the human eye as a residue on the treated surface. In contrast a low VOC cleaning composition with a higher cloud point, above 95° F., or above 90° F. or even above 85° F., depending on the specific formulation, dries in a different manner because dewetting occurs before phase separation, and this creates an irregular pattern of droplets and a visually apparent residue of streaking and filming.

In one embodiment, the present invention teaches a cleaning composition comprising: a. about 0.05-5% by weight of a cationic biocide, b. about 0.01-5% by weight of a non-ionic surfactant, and c. about 0.05-10% by weight of glycol ether solvent, wherein said composition has a cloud point that is less than about 85° F. In another embodiment, the present invention teaches a cleaning composition comprising: a. about 0.05-5% by weight of a cationic biocide, b. about 0.01-5% by weight of an alkoxylate surfactant, and c. about 0.05-10% by weight of solvent, wherein when a 0.5 microliter drop of said composition deposited on a clean silicon surface, forms a circular residue where, within the central 80% of the droplet residue image, there is no position where a 200-micron diameter circle can be placed where it will contain no boundaries between the dark and light portions of the image. In another embodiment, the present invention teaches a method of cleaning a hard surface comprising the following steps: a. creating a cleaning composition comprising: i. about 0.05-5% by weight of a cationic biocide, ii. about 0.01-5% by weight of a nonionic surfactant, and iii. about 0.05-10% by weight of solvent, b. applying said cleaning composition to a substrate; cleaning a hard surface using the substrate loaded with said cleaning composition; and wherein when a 0.5 microliter drop of said composition deposited on a clean silicon surface, forms a circular residue where, within the central 80% of the droplet residue image, there is no position where a 200-micron diameter circle can be placed where it will contain no boundaries between the dark and light portions of the image.

DETAILED DESCRIPTION OF THE INVENTION

Figure 1:
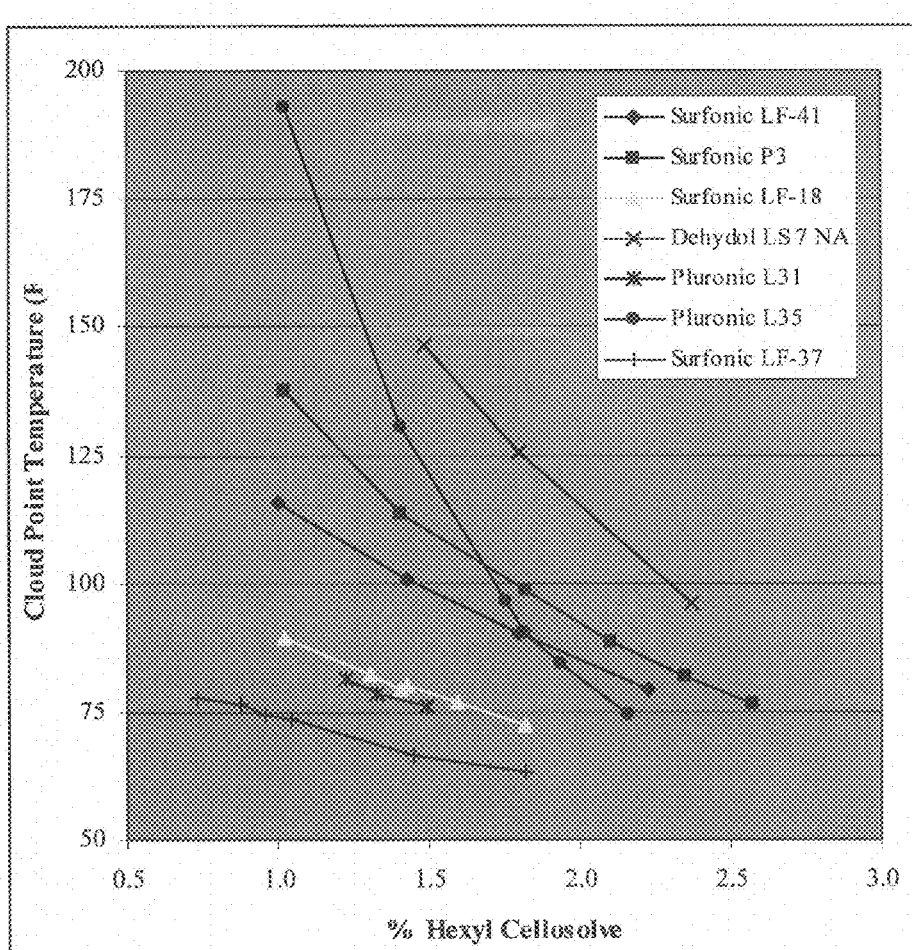
FIG. 1 is a graph showing how different surfactants have varying cloud points depending on the weight % of ethylene glycol monohexyl ether (i.e. hexyl cellosolve) in the composition.

Before describing the present invention in detail, it is to be understood that this invention is not limited to particularly exemplified systems or process parameters that may, of course, vary. It is also to be understood that the terminology used herein is for the purpose of describing particular embodiments of the invention only, and is not intended to limit the scope of the invention in any manner.

All publications, patents and patent applications cited herein, whether supra or infra, are hereby incorporated by reference in their entirety to the same extent as if each individual publication, patent or patent application was specifically and individually indicated to be incorporated by reference.

It must be noted that, as used in this specification and the appended claims, the singular forms "a," "an" and "the" include plural referents unless the content clearly dictates otherwise. Thus, for example, reference to a "surfactant" includes two or more such surfactants.

References herein to "one embodiment", "one aspect" or "one version" of the invention include one or more such embodiment, aspect or version, unless the context clearly dictates otherwise.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In the application, effective amounts are generally those amounts listed as the ranges or levels of ingredients in the descriptions, which follow hereto. Unless otherwise stated, amounts listed in percentage ("%'s") are in active weight percent (based on 100% active) of the active composition alone, unless otherwise indicated.

The term "comprising", which is synonymous with "including," "containing," or "characterized by," is inclusive or open-ended and does not exclude additional, unrecited elements or method steps. See MPEP 2111.03. See, e.g., Mars Inc. v. H.J. Heinz Co., 377 F.3d 1369, 1376, 71 USPQ2d 1837, 1843 (Fed. Cir. 2004) ("like the term 'comprising,' the terms 'containing' and 'mixture' are open-ended."). Invitrogen Corp. v. Biocrest Mfg., L.P., 327 F.3d 1364, 1368, 66 USPQ2d 1631, 1634 (Fed. Cir. 2003) ("The transition 'comprising' in a method claim indicates that the claim is open-ended and allows for additional steps."); Genentech, Inc. v. Chiron Corp., 112 F.3d 495, 501, 42 USPQ2d 1608, 1613 (Fed. Cir. 1997) See MPEP 2111.03. ("Comprising" is a term of art used in claim language which means that the named elements are essential, but other elements may be added and still form a construct within the scope of the claim); Moleculon Research Corp. v. CBS, Inc., 793 F.2d 1261, 229 USPQ 805 (Fed. Cir. 1986); In re Baxter, 656 F.2d 679, 686, 210 USPQ 795, 803 (CCPA 1981); Ex parte Davis, 80 USPQ 448, 450 (Bd. App. 1948). See MPEP 2111.03.

The term "consisting essentially of" as used herein, limits the scope of a claim to the specified materials or steps "and those that do not materially affect the basic and novel characteristic(s)" of the claimed invention. In re Herz, 537 F.2d 549, 551-52, 190 USPQ 461, 463 (CCPA 1976) (emphasis in original). See MPEP 2111.03.

The term "consisting of" as used herein, limits the scope of a claim to the specified materials or steps, indicating that the claim or limitation to which it pertains is closed, not allowing for additional steps or materials.

All numbers expressing quantities of ingredients, constituents, reaction conditions, and so forth used in the specification and claims are to be understood as being modified in all instances by the term "about". Notwithstanding that the numerical ranges and parameters setting forth the broad scope of the subject matter presented herein are approximations, the numerical values set forth in the specific examples are reported as precisely as possible. Any numerical value, however, inherently contains certain errors necessarily resulting from the standard deviation found in their respective testing measurements."

As used herein, the term "disinfect" shall mean the elimination of many or all pathogenic microorganisms on surfaces with the exception of bacterial endospores.

As used herein, the term "sanitize" shall mean the reduction of contaminants in the inanimate environment to levels considered safe according to public health ordinance, or that reduces the bacterial population by significant numbers where public health requirements have not been established. An at least 99% reduction in bacterial population within a 24 hour time period is deemed "significant."

As used herein, the terms "substrate" or "wipe" are intended to include any material on which a cleaning composition may be loaded. In functional application, a substrate is used to clean an article or a surface, as by wiping. Substrates comprise woven or non-woven materials, typically made from a plurality of fibers, as well as sponges, films and similar materials onto which cleaning compositions can be loaded as described herein. The substrate can be used by itself (typically by hand) or attached to a cleaning implement, such as a floor mop, handle, or a hand held cleaning tool, such as a toilet cleaning device.

"Cleaning composition" as used herein, is any fluid and/or solid composition used for cleaning hard and/or soft surfaces. Cleaning means any treatment of a surface which serves to remove or reduce unwanted or harmful materials such as soil, dirt or microbial contamination from a surface, and/or which imparts a desirable or beneficial aesthetic, health or safety effect to the surface such as depositing thereon a fragrance, color or protective coating or film.

"Pre-loaded wipes" as used herein, are wipes which are moistened, such as by wetting the wipe with a liquid composition prior to use by the consumer. "Pre-loaded wipes" as used herein, may also refer to wipes that are moistened prior to packaging in a generally moisture impervious container or wrapper. "Pre-loaded wipes" as used herein may even include dry wipes that are impregnated with liquid and dried prior to packaging or solid actives, including but not limited to cleaning agents. Furthermore, "pre-loaded wipes" as referred to herein may in addition, or in the alternative, include wet wipes that have been pre-moistened with liquid compositions, including but not limited to, liquid compositions, such as cleaning agents or lotions.

The term Volatile Organic Compound (VOC) is meant to mean a compound that falls under one of the following definitions and is not contained on an exemption list. A VOC is any compound with: (a) a vapor pressure (VP)>0.1 mmHg @ 20° C., (b) a boiling point (BP)<216° C., and (c) less than 12 carbons and VP or BP data. The California VOC definition is as follows, "Volatile Organic Compound (VOC)" means any compound containing at least one atom of carbon, excluding carbon monoxide, carbon dioxide, carbonic acid, metallic carbides or carbonates, and ammonium carbonate, and excluding the following: (A) methane, methylene chloride (dichloromethane), 1,1,1-trichloroethane (methyl chloroform), trichlorofluoromethane (CFC-11), dichlorodifluoromethane (CFC-12), 1,1,2-trichloro-1,2,2 trifluoroethane (CFC-113), 1,2-dichloro-1,1,2,2-tetrafluoroethane (CFC-114), chloropentafluoroethane (CFC-115), chlorodifluoromethane (HCFC-22), 1,1,1-trifluoro-2,2-dichloroethane (HCFC-123), 1,1-dichloro-1-fluoroethane (HCFC-141b), 1-chloro-1,1-difluoroethane (HCFC-142b), 2-chloro-1,1,1,2-tetrafluoroethane (HCFC-124), trifluoromethane (HFC-23), 1,1,2,2-tetrafluoroethane (HFC-134), 1,1,1,2-tetrafluoroethane (HFC-134a), pentafluoroethane (HFC-125), 1,1,1-trifluoroethane (HFC-143a), 1,1-difluoroethane (HFC-152a), ethoxy-nonafluorobutane (HFE 7200), cyclic, branched, or linear completely methylated siloxanes, the following classes of perfluorocarbons: 1. cyclic, branched, or linear, completely fluorinated alkanes; 2. cyclic, branched, or linear, completely fluorinated ethers with no unsaturations; 3. cyclic, branched, or linear, completely fluorinated tertiary amines with Consumer Products Regulation 33 no unsaturations; and 4. sulfur-containing perfluorocarbons with no unsaturations and with the sulfur bonds to carbon and fluorine, and (B) the following low-reactive organic compounds which have been exempted by the U.S. EPA: acetone, ethane, methyl acetate, parachlorobenzotrifluoride (1-chloro-4-trifluoromethyl benzene), perchloroethylene (tetrachloroethylene).

In one embodiment of the present invention, the cleaning composition can be loaded onto an absorbent and/or absorbent material, and/or can be used separately from an absorbent and/or absorbent material. The absorbent and/or absorbent material includes, but is not limited to, cleaning wipes, cloths, sponges (e.g., cellulose, synthetic, etc.), paper towels, napkins, rags, mop heads, cleaning pads, towels, brooms, other absorbent cleaning tools, and/or the like.

In another embodiment of the present invention, the cleaning composition is applied to a surface to be cleaned prior to exposing the cleaning composition to an absorbent and/or adsorbent material. In such applications, the cleaning composition is not pre-loaded onto an absorbent and/or adsorbent material, but instead is applied by the user to a surface to be cleaned and then wiped up by the absorbent and/or adsorbent material. As can be appreciated, the absorbent and/or adsorbent material can include some cleaning composition prior to wiping the surface on which the cleaning composition is pre-applied. In another and/or alternative embodiment of the present invention, the cleaning composition is pre-applied to the absorbent and/or adsorbent material for ease of use by the consumer. The cleaning composition can be packaged to be used alone or in combination with other cleaners and/or absorbent or adsorbent materials.

The cleaning composition is typically formulated to clean hard surfaces such as, but not limited to, counter tops; however, the cleaning composition has much broader applications and be used as a clean glass cleaner; appliance cleaner; floor cleaner; rug cleaner; area disinfect, sanitizer, and/or sterilizer; and/or the like. As used herein, the term "hard surfaces" includes, but is not limited to, bathroom surfaces (e.g., floor, tub, shower, mirror, toilet, bidet, bathroom fixtures, etc.), kitchen surfaces (e.g., counter tops, stove, oven, range, sink, refrigerator, microwave, appliances, tables, chairs, cabinets, drawers, floors, etc.), furniture surfaces (e.g., tables, chairs, sofas, love seats, benches, beds, stools, armoires, chests, dressers, display cabinets, clocks, buffet, shades, shutters, entertainment centers, arm rails, lamps, banisters, libraries, cabinets, desks, doors, shelves, couches, beds, carts, pianos, statues and other art, mirrors, racks, fans, light fixtures, pool table, ping pong table, soccer table, card table, etc.), statues, windows, window ledges, tools, utility devices (e.g., telephones, radios, televisions, stereo equipment, CD and DVD players, analog and digital sound devices, palm computers, laptop computers, desktop and tower computers, computer monitors, etc.), automobiles (e.g., interior and exterior surfaces), bicycles, snowmobiles, motorcycles, off-road-vehicles, yard equipment, farm equipment, washing equipment (e.g., power washers, etc.), painting equipment (e.g., electric and air powered painting equipment, etc.), medical and/or dental equipment, marine equipment (e.g., sail boats, power boats, rafts, sail board, canoe, row boats, etc.), toys, writing implements, watches, framed pictures or paintings, books, and/or the like. The cleaning composition can also be used in a variety of industrial and institutional applications. As used herein, the terms "industrial" and "institutional" shall mean the fields of use which include, but are not limited to, contract (e.g., professional) cleaning and disinfecting, retail facilities cleaning and disinfecting, industrial/manufacturing facilities cleaning and disinfecting, office cleaning and disinfecting services, hotel/restaurant/entertainment cleaning and disinfecting, health care (e.g., hospitals, urgent care facilities, clinics, nursing homes, medical/dental offices, laboratories) facilities cleaning and disinfecting, educational facilities cleaning and disinfecting, recreational (e.g., arenas, coliseums, resorts, halls, stadiums, cruise lines, arcades, convention centers, museums, theaters, clubs, family entertainment complexes (e.g., indoor and/or outdoor), marinas, parks) facilities cleaning and disinfecting, food service facilities cleaning and disinfecting, governmental facilities cleaning and disinfecting, public transportation facilities (e.g., airports, airlines, cabs, buses, trains, subways, boats, ports, and their associated properties) cleaning and disinfecting. The cleaning composition can be in concentrated form or unconcentrated form (e.g., ready to use form). When the cleaning composition is not first impregnated on an absorbent or adsorbent material, the cleaning composition can be dispensed and/or sprayed as liquid from a container, as an aerosol from an aerosol container, or as a crystal, powder, paste, or otherwise semi-solid or solid form from a container.

In one aspect of the present invention, the absorbent and/or absorbent material can be at least partially impregnated with the cleaning composition. When the cleaning composition is at least partially loaded or impregnated onto the absorbent and/or absorbent material, the cleaning composition is formulated to have a viscosity that allows such loading. Typically, the viscosity of the cleaning composition is less than about 1000 centipoise ("cps") when the cleaning composition is at least partially loaded or impregnated onto an absorbent and/or absorbent material. The viscosity of the cleaning composition can be greater than 1000 cps when the cleaning composition is used separately from an absorbent and/or absorbent material, and/or is not to be preloaded onto an absorbent and/or absorbent material.

In yet another and/or alternative aspect of the present invention, a kit is provided for cleaning which kit includes the cleaning composition of the present invention. The kit can have an assembly of one or more units, either packaged together or separately. For example, the kit can include cleaning pads and/or wipes, and a container of the cleaning composition. A second example is a kit with cleaning pads and/or wipes, implement and a container of the cleaning composition. A third example is a kit with a refill (concentrated or unconcentrated), a container of ready to use cleaning composition, and cleaning pads and/or wipes that include a superabsorbent material. In one embodiment, the implement that includes a cleaning pad and/or wipe that includes a superabsorbent material, and when used with the cleaning composition provides effective cleaning and good particulate soil removal. In one aspect of this embodiment, the cleaning pad and/or wipe is a disposable and/or does not require rinsing. In another and/or alternative embodiment, the cleaning pad and/or wipe is detachably mounted on the implement. In one aspect of this embodiment, the cleaning pad and/or wipe can be removed and replaced by another cleaning pad and/or wipe. This is especially useful, when the cleaning pad and/or wipe is excessively soiled. The cleaning pad and/or wipe can be removed and replaced with a fresh cleaning pad and/or wipe. In still another and/or alternative aspect of this embodiment, the implement includes a dosing device. The dosing device at least partially delivers the cleaning composition to the surface to be cleaned and/or applies at least a portion of the cleaning composition on the cleaning pad and/or wipe. The dosing device can be battery powered, electrically powered, or hand powered. In still yet another and/or alternative embodiment, a reservoir is provided that is designed to at least partially hold the cleaning composition. In one aspect of this embodiment, the reservoir is detachably mounted on the implement. In another and/or alternative aspect of this embodiment, the reservoir is used in combination with a dosing device.

In yet another and/or alternative aspect of the present invention, the cleaning composition can be at least partially loaded onto an absorbent and/or adsorbent material by a user prior to cleaning. The absorbent and/or adsorbent material can include cleaning wipes, sponges (e.g., cellulose, synthetic, etc.), paper towels, napkins, cleaning pads, cloths, towels, rags, mop heads, and/or the like. In such applications, the cleaning composition is not preloaded or fully preloaded onto an absorbent and/or adsorbent material, thus the cleaning composition is at least partially applied by the user just prior to and/or during the cleaning process. When the cleaning composition is used in such application, the cleaning composition is typically packaged in a separate container or receptacle from the absorbent and/or adsorbent material. During the cleaning process, the cleaning composition is applied to the absorbent and/or adsorbent material. Additionally or alternatively, the cleaning composition can be applied to the surface to be cleaned and the absorbent and/or adsorbent material is used to pick up cleaning composition off the surface to be cleaned and/or spread the cleaning composition on the surface to be cleaned. The cleaning composition can be applied automatically and/or manually applied to the absorbent and/or adsorbent material and/or onto the surface to be cleaned.

In still another and/or alternative aspect of the present invention, the cleaning composition can be applied to a surface to be cleaned prior to exposing the cleaning composition to an absorbent and/or adsorbent material. The absorbent and/or adsorbent material can include cleaning wipes, sponges (e.g., cellulose, synthetic, etc.), paper towels, napkins, cleaning pads, cloths, towels, rags, mop heads, and/or the like. In such applications, the cleaning composition is not preloaded onto an absorbent and/or adsorbent material, but applied by the user to a surface to be cleaned and then wiped up by the absorbent and/or adsorbent material. The cleaning composition can be applied automatically and/or manually applied to the surface to be cleaned.

In still yet another and/or alternative aspect of the present invention, the cleaning composition can be applied and/or added to a surface and/or environment to be cleaned without ever applying the cleaning composition to an absorbent and/or adsorbent material. Examples of such uses of the cleaning composition include, but are not limited to, air fresheners, shampoos, hand lotions/cleaners, cleaners for cleaning internal components of machinery and/or process lines, carpet fresheners, carpet cleaners, cat litter, drain cleaners, toilet cleaners, environment cleaners (e.g., fumigation gas and/or fluid, liquid spray, etc.), and/or the like.

In still another and/or alternative aspect of the present invention, the cleaning composition includes an effective amount of biocide to obtain the desired disinfecting, sanitizing, and/or sterilizing qualities of the cleaning composition. The cleaning composition includes one or more biocides to achieve the desired disinfecting, sanitizing, and/or sterilizing qualities of the cleaning composition. The cleaning composition is typically formulated to partially or completely kill microorganisms such as, but not limited to, bacteria, fungi, molds, mildew, and/or viruses. The antimicrobial efficacy of the cleaning composition can be tailored for a particular household, industrial and/or institutional application, and/or can be formulated to disinfect sanitize, and/or sterilize surfaces in household, industrial and/or institutional environments. In one embodiment, the biocide in the cleaning composition is a cationic biocide. Such cationic biocide includes, but not limited to, quats and/or biguanide compounds. In another and/or alternative embodiment, the biocide in the cleaning composition includes a cationic biocide and at least one other type of biocide.

In still another and/or alternative aspect of the present invention, the cleaning composition includes and/or is used in combination with an effective amount of one or more surfactants. The inclusion of the surfactant in the cleaning composition and/or used in combination with the cleaning composition can improve the cleaning performance of the cleaning composition (e.g., improve wetting properties of the cleaning composition, stabilize components in the cleaning composition, function as an emulsifying agent, reduce filming and/or streaking, etc.).

In still another and/or alternative aspect of the present invention, the cleaning composition can include and/or be used in combination with one or more solvents. The solvent can be used to dissolve various components in the cleaning composition so as to form a substantially uniformly dispersed mixture. In addition to the dispersion and solubilizing functions of the solvent, the solvent can function as a cleaning agent to help loosen and solubilize compounds such as greasy or oily soils from surfaces, a residue inhibiting agent to help reduce residues left behind on a cleaned surface, a detergent agent to assist in the detergency of the cleaning composition, and/or a disinfecting, sanitizing, and/or a sterilizing agent to help eliminate various bacteria and/or viruses on a cleaned surface.

In still yet another and/or alternative aspect of the present invention, the cleaning composition includes and/or is used in combination with water. The water, when used, can be pre-mixed with the other components of the cleaning composition or be partially or fully added to the cleaning composition at the time of or prior to use. The water can include tap water, filtered water, bottled water, spring water, distilled water, deionized water, and/or industrial soft water. The amount of water in and/or combined with the cleaning composition depends on whether the cleaning composition is an aqueous or nonaqueous composition. In one embodiment, the water used in and/or used in combination with the cleaning composition is deionized water and/or industrial soft water. The use of deionized water and/or industrial soft water can reduce the amount of residue formation and can limit the amount of undesirable metal ions in and/or used in combination with the cleaning composition. In another and/or alternative embodiment, the cleaning composition is an aqueous composition, and the water constitutes at least a majority weight percent of the cleaning composition. The amount of water in the cleaning composition is typically less when the cleaning composition is in a concentrated liquid or semi-liquid form, or in a solid form. In another and/or alternative embodiment, the cleaning composition is in a concentrated liquid or semi-liquid form, or in a solid form and is loaded onto a substrate that is activated by water by the end user.

In a further and/or alternative aspect of the present invention, the cleaning composition includes and/or is used in combination with one or more adjuncts. The adjuncts include, but are not limited to, buffering and pH adjusting agents, fragrances or perfumes, waxes, dyes and/or colorants, solubilizing materials, stabilizers, thickeners, defoamers, hydrotropes, lotions and/or mineral oils, enzymes, bleaching agents, cloud point modifiers, preservatives, ion exchangers, alkalies, anticorrosion materials, antiredeposition materials, optical brighteners, chelating agents, enzymes, whiteners, brighteners, antistatic agents, sudsing control agents, hydrotropes, bleach precursors, soil removal agents, soil release agents, softening agents, opacifiers, inert diluents, graying inhibitors, stabilizers, and/or polymers.

The advantages of the cleaning composition and cleaning substrate of the present invention are that the composition has low levels of VOCs, good cleaning and disinfecting performance and low streaking and filming on hard surfaces. Other advantages will become apparent to those skilled in the art upon reading and following the description of the invention taken together with the accompanying figures.

DETAILED DESCRIPTION OF THE PREFERRED EMBODIMENTS

The cleaning composition of the present invention can be used independently from or in conjunction with an absorbent and/or adsorbent material. For instance, the cleaning composition is formulated to be used in conjunction with a cleaning wipe, sponge (e.g., cellulose, synthetic, etc.), cleaning pad, paper towel, napkin, cloth, towel, rag, mop head, squeegee, and/or other cleaning device that includes an absorbent and/or adsorbent material. The cleaning composition can be formulated to be loaded onto and/or used in combination with an absorbent and/or adsorbent material (e.g., cleaning wipe, cleaning pad, mop head, cloth, towel, etc.) to clean hard surfaces. The cleaning composition can also or alternatively be formulated to clean fabrics (e.g., clothing, carpet, curtains, rugs, etc.). The cleaning composition can also or alternatively be formulated to disinfect and/or sanitize various areas and things (e.g., rooms, pet litter, medical equipment, etc.)

The cleaning composition can also or alternatively be formulated for use in personal hygiene products (e.g., hand cleaners, body lotions, shampoos, hair conditioners, etc.). The cleaning composition is particularly applicable for use with hard surfaces. Such surfaces include, but are not limited to, windows, doors, counter tops, floor, sinks, toilets, showers, kitchen appliances, and the like. When cleaning hard surfaces, an important goal is to not only clean, disinfect, sanitize, and/or sterilize the hard surface, but to also reduce filming and streaking on the hard surface. It is also desirable for the cleaned hard surface to not be sticky. The cleaning composition is formulated to clean, disinfect, sanitize, and/or sterilize hard surfaces, and to reduce filming and streaking on the hard surface without leaving a sticky surface on the cleaned hard surface.

The cleaning composition can be in concentrated form or ready-to-use form. The cleaning composition can be in gas, liquid, paste, gel, or solid form. The cleaning composition can be dispensed from a liquid container, an aerosol container, a container for holding crystals or a paste, and the like. The cleaning composition can be preloaded onto an absorbent and/or adsorbent material, and/or used in combination with an absorbent and/or adsorbent material.

The basic components of the cleaning composition for hard surfaces include:
(i) cationic biocide;
(ii) solvent with less than 5% VOCs
(iii) surfactant.

Additional components can be included in and/or used in combination with the cleaning composition to add one or more attributes to the cleaning composition and/or to enhance the attributes of the cleaning composition.

A. The Cationic Biocide

The biocide in the cleaning composition includes a cationic compound. The cationic biocide typically includes one or more biguanide compounds and/or quats. Biguanide compounds are desirable in that such compounds have broad spectrum antimicrobial or germicidal properties. The biguanide compounds are also less irritating to skin, and produce less streaking and residue when applied to a hard surface. As a result, the cleaning composition feels drier after being applied resulting in higher consumer satisfaction. A variety of different biguanide compounds can be used in the cleaning composition. The biguanide compounds that can be used in the cleaning composition include, but are not limited to, compounds have the following general formula:

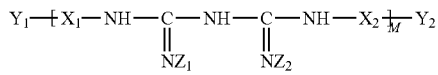

where X1 and X2 are either a hydrogen or any aliphatic, cycloaliphatic, aromatic, substituted aliphatic, substituted aromatic, heteroaliphatic, heterocyclic, and/or heteroaromatic compound. X1 and X2 can be the same or different. Y1 and Y2 are any aliphatic, cycloaliphatic, aromatic, substituted aliphatic, substituted aromatic, heteroaliphatic, heterocyclic, and/or heteroaromatic compound. Y1 and Y2 can be the same or different. M is a number equal to or greater than 1. Typically, M has an average value such that the molecular weight of biguanide compounds is about 1000-1400; however, the molecular can be higher or lower. Generally M is about 2-20. N is a nitrogen atom. Z1 and Z2 are either a hydrogen or a salt. Z1 and Z2 can be the same of different.

Specific examples of these compounds include, but are not limited to, polyhexamethylene biguanide hydrochloride, p-chlorophenyl biguanide; and 4-chlorobenzhydryl biguanide. In still yet another and/or alternative aspect of this embodiment, the biguanide compound includes, but is not limited to, halogenated hexidine such as, but not limited to, chlorhexidine (1,1'-hexamethylene-bis-5-(4-chlorophenyl biguanide) and its salts. In addition or alternatively, the biguanide compounds include, but are not limited to, halogenated hexidine and its salts. The salts include, but are not limited to, salts with an inorganic acid, such as hydrochloride, hydrofluoride, nitrate, sulfate and/or phosphate, and/or salts with an organic acid such as, but not limited to, carboxylic acid, acetate, benzoate, tartrate, adipate, lactate, formate, maleate, glutamate, ascorbate, citrate, gluconate, oxalate, succinate, pamoate, salicylate, isethionate, succinamate, mono-diglycolate, dimethanesulfonate, di-isobutyrate, and/or glucoheptonate. Examples of salts of chlorhexidine include, but are not limited to, chlorhexidine diphosphanilate, chlorhexidine digluconate, chlorhexidine diacetate, chlorhexidine dihydrochloride, chlorhexidine dichloride, chlorhexidine gluconate, chlorhexidine dihydroiodide, chlorhexidine diperchlorate, chlorhexidine dinitrate, chlorhexidine sulfate, chlorhexidine sulfite, chlorhexidine thiosulfate, chlorhexidine di-acid phosphate, chlorhexidine difluorophosphate, chlorhexidine diformate, chlorhexidine dipropionate, chlorhexidine di-iodobutyrate, chlorhexidine di-valerate, chlorhexidine dicaproate, chlorhexidine malonate, chlorhexidine succinate, chlorhexidine malate, chlorhexidine tartrate, chlorhexidine dimonoglycolate, chlorhexidine monodiglycolate, chlorhexidine dilactate, chlorhexidine di-alpha-hydroxyisobutyrate, chlorhexidine diglucoheptonate, chlorhexidine di-isothionate, chlorhexidine dibenzoate, chlorhexidine dicinnamate, chlorhexidine dimandelate, chlorhexidine di-isophthalate, chlorhexidine di-2-hydroxynapthoate, and chlorhexidine embonate. Additional examples of biguanide compounds which can be used in the cleaning composition are disclosed in U.S. Pat. Nos. 2,684,924; 2,990,425; 3,468,898; 4,022,834; 4,053,636; 4,198,392; 6,143,244; 6,143,281; and 6,153,568; EPC 24,031; and DE 1,964,196; DE 2,212,259; and DE 2,627,548, which are incorporated herein by reference.

The biguanide compound content of the cleaning composition is generally maintained at least above 0.0005 weight percent, and more generally above about 0.02 weight percent and less than about 10 weight percent; however, higher or lower biguanide compound contents can be used. In one aspect of this embodiment, the biguanide compound content of the cleaning composition is about 0.05-5 weight percent. In another aspect of this embodiment, the biguanide compound content of the cleaning composition is about 0.08-5 weight percent. In still another aspect of this embodiment, the biguanide compound content of the cleaning composition is about 0.1-2 weight percent. In yet another aspect of this embodiment, the biguanide compound content of the cleaning composition is about 0.1-1 weight percent. In still yet another aspect of this embodiment, the biguanide compound content of the cleaning composition is about 0.15-0.8 weight percent. In a further aspect of this embodiment, the biguanide compound content of the cleaning composition is about 0.175-0.6 weight percent. In yet a further aspect of this embodiment, the biguanide compound content of the cleaning composition is about 0.2-0.5 weight percent. In still a further aspect of this embodiment, the biguanide compound content of the cleaning composition is about 0.25-0.4 weight percent.

The weight percentage range for the biguanide compound in the cleaning composition is selected to disinfect, sanitize, and/or sterilize most common household, institutional, and industrial hard surfaces. Common types of bacteria that are at least partially destroyed by biguanide compounds in the cleaning composition include, but are not limited to, *Staphylococcus aureus* (Staph), *Klebsiella pneumonia* (Kleb), *Salmonella choleraesuis* (Salmonella), *Pseudomonas aeruginosa, Pserratia marcescens*, Influenza A2, *Candida albicans, Fusarium solani*, common viruses and/or fungi.

In yet another and/or alternative aspect of the present invention, the cleaning composition includes a cationic biocide that includes one or more quats. The cationic biocide in the cleaning composition can primarily include one or more quats, and/or include one or more other cationic biocides in combination with the one or more quats. Such other cationic biocides include, but are not limited to, biguanide compounds. Similar to biguanide compounds, quats are also capable of imparting broad spectrum antimicrobial or germicidal properties to the cleaning composition. In another and/or alternative embodiment, the general structure for the one or more quats that can be included in the cleaning composition is:

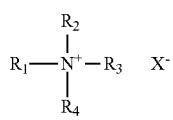

wherein X is an anion such as, but not limited to, a halide, acetate, nitrite, a lower alkosulfate, carbonate and/or an alkyl carboxylate; and R1-R4 are straight chain, branched chain and/or cyclic chain groups. R1-R4 can be the same or different. In one aspect of this embodiment, one or more of the quats included in the cleaning composition have at least one higher molecular weight group and at least one lower molecular weight group linked to a common, positively charged nitrogen atom. The one or more higher molecular weight groups include, but are not limited to, higher alkyl groups containing about 6-30 carbon atoms that are branched, unbranched, saturated and/or unsaturated. The one or more lower molecular weight groups include, but are not limited to, 1-12 carbon atoms that are branched, unbranched, saturated, and/or unsaturated. Specific lower molecular weight substituents include, but are not limited to, alkyls of 1 to 4 carbon atoms (e.g., methyl and ethyl), alkyl ethers, hydroxyalkyls, and/or benzyls. One or more of the higher and/or lower molecular weight substituents can include, or can be replaced by, an aryl moiety. Specific aryl moieties include, but are not limited to, benzyl, ethyl benzyl and/or phenyl. In another and/or alternative aspect of this embodiment, an electrically balancing anion (counterion) is linked to the positively charged nitrogen atom. Specific anions include, but are not limited to, bromide, sulfate, iodide, alkycarboxylate, methosulfate, ethosulfate, phosphate, carboxylic acid, or chloride. In still another and/or alternative aspect of this embodiment, specific quats that can be used in the cleaning formulation include, but are not limited to, alkyl ammonium halides such as lauryl trimethyl ammonium chloride and dilauryl dimethyl ammonium chloride; alkyl aryl ammonium halides such as octadecyl dimethyl benzyl ammonium bromide; ethyl dimethyl stearyl ammonium chloride, trimethyl stearyl ammonium chloride, trimethyl cetyl ammonium chloride, dimethyl ethyl lauryl ammonium chloride, dimethyl propyl myristyl ammonium chloride, dinonyl dimethyl ammonium chloride, didecyl dimethyl ammonium chloride, diundecyl dimethyl ammonium chloride, didecyl dimethyl ammonium chloride, dinonyly ethyl ammonium chloride, dimethyl ethyl benzyl ammonium chloride, 3-(trimethyxyosilyl)propyldidecylmethyl ammonium chloride, 3-(trimethoxysilyl)propyloctadecycdimethyl ammonium chloride, dimethyl dioctyl ammonium chloride, didecyl dimethyl ammonium chloride, didodecyl dimethyl ammonium chloride, dimethyl ditetradecyl ammonium chloride, dihexadecyl dimethyl ammonium chloride, dimethyl dioctadecyl ammonium chloride, decyl dimethyl octyl ammonium chloride, dimethyl dodecyloctyl ammonium chloride, benzyl decyl dimethyl ammonium chloride, benzyl dimethyl dodecyl ammonium chloride, benzyl dimethyl tetradecyl ammonium chloride, decyl dimethyl (ethyl benzyl)ammonium chloride, decyl dimethyl (dimethyl benzyl)-ammonium chloride, (chlorobenzyl)-decyl dimethyl ammonium chloride, decyl-(dichlorobenzyl)-dimethyl ammonium chloride, benzyl didecyl methyl ammonium chloride, benzyl didocyl methyl ammonium chloride, benzyl ditetradecyl methyl ammonium chloride, benzyl dodecyl ethyl methyl ammonium chloride, and N-alkyl Dimethyl Benzyl Ammonium Chloride, and N-alkyl Ethylbenzyl Ammonium Chloride and/or the like.

Nonlimiting types of quat that can be used in the cleaning composition include an alkyldimethylbenzylammonium quat, an alkyldimethylethylbenzylammonium quat and/or an alkyldimethylammonium quat. Nonlimiting specific quat that can be used in the cleaning composition is a combination of n-alkyldimethylbenzylammonium chloride (C14-60%, C16-30%, C12-5%, C16-5%) and n-alkyldimethylethylbenzylammonium chloride (C12-68%, C14-32%); available as BTC 2125M from Stepan. Other suitable alkyldimethylbenzyl ammonium chlorides are available such as Barquat MB-50 from Lonza; di(C6-C14)alkyl di(C1-4 alkyl and/or hydroxyalkyl) quaternary ammonium compounds such as Bardac 2050 and/or 2250 from Lonza, (3-chloroallyl) hexaminium chlorides such as Dowicide and Dowicil available from Dow; benzethonium chloride such as Hyamine, methylbenzethonium chloride represented by Hyamine IOX, cetylpyridinium chloride such as Cepacol chloride available from of Merrell Labs.

When one or more quats are included in the cleaning composition, the quat content of the cleaning composition is typically maintained above about 0.0005 weight percent and less than about 10 weight percent; preferably 0.01 to about 5% by weight; or 0.01 to about 2% by weight or even 0.01 to about 1% by weight. In another and/or alternative embodiment, the quat content of the cleaning composition is greater than about 0.04 weight percent of the cleaning composition when the quat functions as the primary biocide in the cleaning composition. As can be appreciated, when other biocides are included with the one or more quats in the cleaning composition, the quat content can be lower than about 0.04 weight percent of the cleaning composition. The weight percentage range for the quat in the cleaning composition is selected to disinfect, sanitize, and/or sterilize most common household, institutional, and industrial hard surfaces. Common types of bacteria that are at least partially destroyed by the quat in the cleaning composition include, but are not limited to, *Staphylococcus aureus* (Staph), *Klebsiella pneumonia* (Kleb), *Salmonella choleraesuis* (Salmonella), *Pseudomonas aeruginosa, Pserratia marcescens*, Influenza A2, *Candida albicans, Fusarium solani*, common viruses and/or fungi.

The upper limit to the quat content of the cleaning composition can be significantly greater than about 0.04 weight percent; however, the quat content is typically limited by economic cost considerations, local, state and/or federal regulatory restrictions, formula solubility requirements, streaking properties of the cleaning composition, skin irritation considerations, and/or the intended use of the cleaning composition. Typically, the quat content of the cleaning composition is no more than about 5 weight percent. In addition, a quat content exceeding about 5 weight percent may be subject to strict local, state and/or federal regulations due to the toxicity of the cleaning composition. In one aspect of this embodiment, the quat content of the cleaning composition is about 0.05-5 weight percent. In another aspect of this embodiment, the quat content of the cleaning composition is about 0.08-5 weight percent. In still another aspect of this embodiment, the quat content of the cleaning composition is about 0.1-2 weight percent. In yet another aspect of this embodiment, the quat content of the cleaning composition is about 0.1-1 weight percent. In still yet another aspect of this embodiment, the quat content of the cleaning composition is about 0.15-0.8 weight percent. In a further aspect of this embodiment, the quat content of the cleaning composition is about 0.175-0.6 weight percent. In yet a further aspect of this embodiment, the quat content of the cleaning composition is about 0.2-0.5 weight percent. In still a further aspect of this embodiment, the quat content of the cleaning composition is about 0.25-0.4 weight percent.

In yet another and/or alternative aspect of the present invention, the cleaning composition includes and/or is used in combination with one or more additional biocides used in combination with the biguanide compound and/or quat. Such biocides can include, but are not limited to, alcohols, peroxides, boric acid and borates, chlorinated hydrocarbons, organometallics, halogen-releasing compounds, mercury compounds, metallic salts, pine oil, organic sulfur compounds, iodine compounds, silver nitrate, quaternary phosphate compounds, and/or phenolics.

B. The Solvent

The solvent used in and/or in combination with the cleaning composition is selected to at least partially dissolve into solution the biguanide compound, quat, and/or other organic compounds in the cleaning composition. The use of certain solvents can also improve the cleaning, biocidal and/or detergency properties of the cleaning composition. Generally, the one or more solvents include in and/or used in combination with the cleaning composition include, but are not limited to, C1-6 alkanols, C1-6 diols, C1-10 alkyl ethers of alkylene glycols, C3-24 alkylene glycol ethers, and/or polyalkylene glycols. The solvent content of the cleaning composition is generally maintained above about 0.1 weight percent and generally less than about 10 weight percent; however, higher or lower solvent contents can be used. Typically, the solvent content of the cleaning composition is about 0.5-5 weight percent. The low-VOC solvents such as, but not limited to glycol ethers are particularly desirable because they help the cleaning compositions meet the strict local, state and/or federal regulations for increasingly low VOC requirements. In one embodiment of the invention the first solvent is a low-VOC solvent which is about 0.1-5% by weight; or 0.1-3% by weight or even 0.1-2% by weight of the cleaning composition. In one embodiment of the invention, the low-VOC solvent includes ethylene glycol monohexyl ether.

Various solvent combinations in the cleaning composition can also facilitate in the reduction of filming and/or streaking. One particular solvent combination that results in reduced filming and/or streaking is a solvent combination that includes a first solvent comprising a glycol ether and a second solvent selected from the group consisting of: alcohols, diols, C1-10 alkyl ethers of alkylene glycols, C3-24 alkylene glycol ethers; polyalkylene glycols, short chain carboxylic acids, short chain esters, isoparaffinic hydrocarbons, mineral spirits, alkylaromatics, terpenes, terpene derivatives, terpenoids, terpenoid derivatives, formaldehyde, pyrrolidones, water, and any mixtures or combinations thereof. In one embodiment of the invention, the second solvent is about 0.1-5% by weight; or 0.1-3% by weight or 0.1-2% by weight; or even less than 1% by weight of the cleaning composition. Suitable solvents that can be used in the cleaning composition include, but are not limited to, methanol, ethanol, isopropanol, propanol, butyl alcohol, sec-butyl alcohol, isobutyl alcohol, tert-butyl alcohol, pentyl alcohol, tert-pentyl alcohol, 2-pentanol, 3-pentanol, neopentyl alcohol, allyl, crotyl, methylvinylcarbinol, ethyl ether, -propyl ether, isopropyl ether, -butyl ether, vinyl ether, allyl ether, ethyleneglycol methylether, ethyleneglycol ethylether, ethyleneglycol propylether, propyleneglycol methylether, propyleneglycol ethylether, ethyleneglycol methyletheracetate, and/or propyleneglycol methyletheracetate, ethylene glycol, propylene glycol, butanediol, methylpropanediol, ethyleneglycol butylether, ethyleneglycol hexylether, ethyleneglycol ethylhexylether, diethyleneglycol methylether, diethyleneglycol ethylether, diethyleneglycol propylether, diethyleneglycol butylether, propyleneglycol-propylether, propyleneglycol t-butylether, propyleneglycol-butylether, dipropyleneglycol methylether, dipropyleneglycol ethylether, dipropyleneglycol-propylether, dipropyleneglycol t-butylether, dipropyleneglycol-butylether, tripropyleneglycol methylether, tripropyleneglycol-butylether, ethyleneglycol ethyletheracetate, propyleneglycol ethyletheracetate, ethyleneglycol butyletheracetate, propyleneglycol butyletheracetate, diethyleneglycol methyletheracetate, dipropyleneglycol methyletheracetate, diethyleneglycol ethyletheracetate, dipropyleneglycol ethyletheracetate, diethyleneglycol butyletheracetate, dipropyleneglycol butyletheracetate, ethylene glycol monohexyl ether and/or N-methyl-2-pyrrolidone.

C. The Surfactant

The surfactant used in and/or in combination with the cleaning composition is selected to improve the cleaning performance of the cleaning composition. The surfactant can also reduce the amount of perceived filming and/or streaking of the cleaning composition. The surfactant also can provide detergency to the cleaning composition to facilitate in the removal of soil from the hard surface. The surfactant also can reduce the amount of redeposition of soils onto the hard surface.

In one aspect of the invention, the surfactant is a non-ionic surfactant. In one embodiment the surfactant includes, but is not limited to, at least one lauryl sulfate, lauryl ether sulfate, cocamidopropylbetaine, alkyl polyglycoside, ethoxylated alcohol, propoxylated alcohol, fluorosurfactant, amine oxide and any combinations or mixtures thereof. In one particular formulation, the surfactant in and/or used in combination with the cleaning composition includes alkyl polyglycosides, ethoxylated alcohol, fluorosurfactant, ethylene oxide and propylene oxide alcohols (EO-PO surfactants), polyglycol ether and/or amine oxides. Specific kinds of surfactants that can be included in the cleaning composition are: polyglycol ether surfactants sold under the brand Tergitol by Dow, alcohol ethoxylates sold under the brand Ecosurf by Dow, ethoxylated alcohol sold under the Surfonic by Huntsman, and/or EO-PO surfactants sold under the brand Pluronic by BASF.

A variety of surfactants can be used in and/or use in combination with the cleaning composition. Such surfactants include, but are not limited to, nonionic, semi-polar, anionic, cationic, zwitterionic, and/or amphoteric surfactants. Many of these surfactants are described in McCutcheon's Emulsifiers and Detergents (1997), Kirk-Othmer, Encyclopedia of Chemical Technology, 3rd Ed., Volume 22, pp. 332-432 (Marcel-Dekker, 1983), and McCutcheon's Soaps and Detergents (N. Amer. 1984), the contents of which are hereby incorporated by reference. Typically the surfactant is partially or fully soluble in water.

In one embodiment of the invention, the cleaning composition only contains nonionic surfactants. In another embodiment, the surfactant includes, but is not limited to, glycoside, glycols, ethylene oxide and mixed ethylene oxide/propylene oxide adducts of alkylphenols, the ethylene oxide and mixed ethylene oxide/propylene oxide adducts of long chain alcohols or of fatty acids, mixed ethylene oxide/propylene oxide block copolymers, esters of fatty acids and hydrophilic alcohols, sorbitan monooleates, alkanolamides, soaps, alkylbenzene sulfonates, olefin sulfonates, paraffin sulfonates, propionic acid derivatives, alcohol and alcohol ether sulfates, phosphate esters, amines, amine oxides, alkyl sulfates, alkyl ether sulfates, sarcosinates, sulfoacetates, sulfosuccinates, cocoamphocarboxy glycinate, salts of higher acyl esters of isethionic acid, salts of higher acyl derivatives of taurine or methyltaurine, phenol poly ether sulfates, higher acyl derivatives of glycine and methylglycine, alkyl aryl polyether alcohols, salts of higher alkyl substituted imadazolinium dicarboxylic acids, ferchorics, tannics, naphthosulfonates, monochloracetics anthraflavinics, hippurics, anthranilics, naphthoics, phthalics, carboxylic acid salts, acrylic acids, phosphates, alkylamine ethoxylates, ethylenediamine alkoxylates, betaines, sulfobetaines, and/or imidazolines.

The surfactant content in and/or used in combination with the cleaning composition is generally at least about 0.001 weight percent of the cleaning composition. In another aspect of this embodiment, the surfactant content in and/or used in combination with the cleaning composition is about 0.01-5 weight percent. Typically the surfactant is at least about 0.05 weight percent and less than about 2 weight percent of the cleaning composition, and more typically about 0.1-2 weight percent of the cleaning composition. In yet a further aspect of this embodiment, the surfactant content in and/or used in combination with the cleaning composition is about 0.15-1.5 weight percent. In still yet a further aspect of this embodiment, the surfactant content in and/or used in combination with the cleaning composition is about 0.2-1.5 weight percent. In another aspect of this embodiment, the surfactant content in and/or used in combination with the cleaning composition is about 0.2-1.25 weight percent. In yet another aspect of this embodiment, the surfactant content in and/or used in combination with the cleaning composition is about 0.5-1.25 weight percent. In still another aspect of this embodiment, the surfactant content in and/or used in combination with the cleaning composition is about 0.1-1 weight percent. In still yet another aspect of this embodiment, the surfactant content in and/or used in combination with the cleaning composition is about 0.15-0.8 weight percent. In a further aspect of this embodiment, the surfactant content in and/or used in combination with the cleaning composition is about 0.2-0.4 weight percent. In yet a further aspect of this embodiment, the surfactant content in and/or used in combination with the cleaning composition is less than about 0.5 weight percent.

D. Water

The cleaning composition typically includes water. When the cleaning composition is a liquid, water based, ready-to-use cleaner, the water content of the cleaning composition is generally over 70 weight percent of the cleaning composition. Typically, the liquid ready-to-use cleaning composition includes at least about 90 weight percent water; however, higher or lower water contents can be used. When the cleaning composition is a liquid, non-water based, ready-to-use cleaner, the water content of the cleaning composition is generally less than about 30 weight percent of the cleaning composition, and typically less than about 15 weight percent of the cleaning composition.

The water used in the cleaning composition is typically deionized water and/or industrial soft water so as to reduce residue formation and limit the amount of undesirable metal ions in the cleaning composition; however, other types of water can be used (e.g., tap water, spring water, filtered water, etc.).

E. Biocide Release Agent

When the cleaning composition is loaded onto an absorbent or adsorbent material, and/or is to be used with an absorbent or adsorbent material, a biocide release agent is optionally included in and/or used with the cleaning composition to improve the release of the biguanide compound, quat, and/or other cationic biocides in the cleaning composition from the absorbent and/or adsorbent material. The biocide release agent used in the cleaning composition typically includes a cationic compound designed to compete with the cationic biocide (e.g., biguanide compound, quat, etc.) for anionic species sites on the absorbent and/or adsorbent material (e.g., sponges (e.g., cellulose, synthetic, etc.), paper towels, cleaning pads, cleaning wipes, napkins, cloths, towels, rags, mop heads, squeegee). The cationic biocide release agent typically includes a cationic salt. Generally, a commonly available salt is used so as to minimize the raw material cost of the cleaning composition. In addition, a salt having a relatively high ionic strength per mole of salt is selected to minimize the amount of salt needed in the cleaning composition so as to also minimizing the raw material cost of the cleaning composition. Nonlimiting examples of salts that can be used as a biocide release agent in and/or in combination with the cleaning composition include potassium citrate, sodium citrate, magnesium sulphate, sodium chloride, ammonium chloride, and/or potassium chloride. Generally, the one or more salts are added to and/or used in combination with the cleaning composition in an amount to cause over about 50% of the cationic biocide to be released from the absorbent or adsorbent material when used to clean a hard surface. Generally, the ionic strength of the one or more salts that make up the biocide release agent used in and/or used in combination with the cleaning composition is about $1\times10$-2-2 mol/l, and the weight percent of the salt used in and/or in combination with the cleaning composition is about 0-5 weight percent; preferably 0-2%; most preferably less than 1% by weight.

F. Additional Anti-Microbial Compound

One or more additional anti-microbial compounds can be included in and/or used in combination with the cleaning composition to enhance the biocidal efficacy of the cleaning composition. Such anti-microbial compounds include, but are not limited to, diisobutylphenoxyethoxyethyl dimethylbenzyl ammonium chloride, commercially available as Hyamine 1622 from Lonza. Other anti-microbial compounds include, but are not limited to, alcohols, peroxides, boric acid and borates, chlorinated hydrocarbons, organometallics, halogen-releasing compounds, mercury compounds, metallic salts, pine oil, essential oils, organic sulfur compounds, iodine compounds, silver nitrate and other silver compounds, quaternary phosphate compounds, and/or phenolics.

G. Additional Adjuvants

The cleaning composition may optionally include and/or be used in combination with one or more additional adjuncts. The adjuncts include, but are not limited to, fragrances or perfumes, waxes, dyes and/or colorants, solubilizing materials, stabilizers, thickeners, defoamers, hydrotropes, buffers, builders, lotions and/or mineral oils, enzymes, bleaching agents, cloud point modifiers, and/or preservatives. A variety of builder detergents can be used in and/or used in combination with the cleaning composition. Such builder detergents include, but are not limited to, phosphate-silicate compounds, zeolites, alkali metal, ammonium and substituted ammonium polyacetates, mono-, di-, and tri-alkali salts of nitrilotriacetic acid, carboxylates, aluminosilicate materials, silicates, polycarboxylates, zeolites, carbonates, phosphates, bicarbonates, polyphosphates, amines, alkanolamines, aminopolycarboxylates, polyhydroxysulfonates, starch derivatives, ethylenediamine tetraacetate, and/or metal ion sequestrants (e.g., aminopolyphosphonates such as, but not limited to, ethylenediamine tetramethylene phosphonic acid and diethylene triamine pentamethylenephosphonic acid). In one embodiment, the builder detergent includes polyacetate and/or polycarboxylate compounds. In one aspect of this embodiment, the polyacetate and/or polycarboxylate compounds include, but are not limited to, sodium, potassium, lithium, ammonium, and substituted ammonium salts of ethylenediamine tetraacetic acid, ethylenediamine triacetic acid, ethylenediamine tetrapropionic acid, diethylenetriamine pentaacetic acid, nitrilotriacetic acid, oxydisuccinic acid, iminodisuccinic acid, mellitic acid, polyacrylic acid or polymethacrylic acid and copolymers, benzene polycarboxylic acids, gluconic acid, sulfamic acid, oxalic acid, phosphoric acid, phosphonic acid, organic phosphonic acids, acetic acid, and citric acid. In one embodiment, the buffering and pH adjusting agents, when used, include, but are not limited to, organic acids, mineral acids, alkali metal and alkaline earth salts of silicate, metasilicate, polysilicate, borate, carbonate, carbamate, phosphate, polyphosphate, pyrophosphates, triphosphates, tetraphosphates, ammonia, hydroxide, monoethanolamine, monopropanolamine, diethanolamine, dipropanolamine, triethanolamine, and/or 2-amino-2-methylpropanol. The buffering agent can be an active detergent in its own right, and/or can be a low molecular weight, organic or inorganic material used for maintaining the desired pH. The buffer can be alkaline, acidic or neutral. Non-limiting examples of buffering agents include nitrogen-containing materials (e.g., lysine; lower alcohol amines like mono-, di-, and tri-ethanolamine; tri(hydroxymethyl)amino methane; 2-amino-2-ethyl-1,3-propanediol; 2-amino-2-methyl-propanol; 2-amino-2-methyl-1,3-propanol; disodium glutamate; methyl diethanolamide; 2-dimethylamino-2-methylpropanol; 1,3-bis(methylamine)-cyclohexane; 1,3-diamino-propanol N,N'-tetra-methyl-1,3-diamino-2-propanol; N,N-bis (2-hydroxyethyl)glycine; tris(hydroxymethyl)methyl glycine; ammonium carbamate; citric acid; acetic acid; ammonia; alkali metal carbonates; and/or alkali metal phosphates). For additional buffers that can be used, see McCutcheon's EMULSIFIERS AND DETERGENTS, North American Edition, 1997, McCutcheon Division, MC Publishing Company which is incorporated herein by reference. In yet another and/or alternative embodiment, the solubilizing materials, when used, include, but are not limited to, hydrotropes (e.g., water soluble salts of low molecular weight organic acids such as the sodium and/or potassium salts of xylene sulfonic acid). In another and/or alternative embodiment, the acids, when used, include, but are not limited to, organic hydroxy acids, citric acids, keto acid, and the like. In still another and/or alternative embodiment, thickeners, when used, include, but are not limited to, polyacrylic acid, xanthan gum, calcium carbonate, aluminum oxide, alginates, guar gum, methyl, ethyl, clays, and/or propylhydroxycelluloses. In yet another and/or alternative embodiment, defoamers, when used, include, but are not limited to, silicones, aminosilicones, silicone blends, and/or silicone/hydrocarbon blends. In yet a further and/or alternative embodiment, bleaching agents, when used, include, but are not limited to, peracids, perborates, percarbonates, chlorine-generating substances (e.g., chloroisocyanurates hypohalite sources), hydrogen peroxide, and/or sources of hydrogen peroxide. In still a further and/or alternative embodiment, preservatives, when used, include, but are not limited to, mildewstats or bacteriostats, methyl, ethyl and propyl parabens, short chain organic acids (e.g., acetic, lactic and/or glycolic acids), bisguanidine compounds (e.g., Dantagard and/or Glydant) and/or short chain alcohols (e.g., ethanol and/or IPA). In one aspect of this embodiment, the mildewstats or bacteriostats include, but are not limited to, mildewstats (including non-isothiazolone compounds) include Kathon GC, a 5-chloro-2-methyl-4-isothiazolin-3-one, Kathon ICP, a 2-methyl-4-isothiazolin-3-one, and a blend thereof, and Kathon 886, a 5-chloro-2-methyl-4-isothiazolin-3-one, all available from Rohm and Haas Company; Bronopol, a 2-bromo-2-nitropropane-1,3-diol, from Boots Company Ltd.; Proxel CRL, a propyl-p-hydroxybenzoate, from ICI PLC; Nipasol M, an o-phenyl-phenol, Na+ salt, from Nipa Laboratories Ltd.; Dowicide A, a 1,2-Benzoisothiazolin-3-one, from Dow Chemical Co.; and Irgasan DP 200, a 2,4,4'-trichloro-2-hydroxydiphenylether, from Ciba-Geigy A.G.

In still a further and/or alternative aspect of the present invention, the cleaning composition has a neutral or alkaline pH. Various compounds (e.g., adjuncts, biocides, etc.) can be added to and/or used in combination with the cleaning composition to control the pH of the cleaning composition. In one embodiment, the pH of the cleaning composition is about neutral. In one aspect of this embodiment, the pH of the cleaning composition is between about 5-9. In another aspect of this embodiment, the pH of the cleaning composition is between about 6-8.

H. The Absorbent and/or Adsorbent Material

The cleaning composition, when used to clean hard surfaces, is generally used in conjunction with one or more absorbent and/or adsorbent materials. The cleaning composition can be sprayed and/or poured onto a hard surface to be cleaned and an absorbent and/or adsorbent material such as, but not limited to, a sponge, mop head, cloth, towel, and the like is then used to spread the cleaning composition on the hard surface and/or clean the hard surface. Additionally or alternatively, the cleaning composition is at least partially loaded on the absorbent and/or adsorbent material prior to the absorbent and/or adsorbent material at least partially applying the cleaning composition onto the hard surface and/or cleaning the hard surface.

The present invention also contemplates the pre-loading of the cleaning composition on a cleaning pad and/or cleaning wipe. In one embodiment, the cleaning wipe includes, but is not limited to, a woven and/or a nonwoven material. In one aspect of this embodiment, the nonwoven material includes, but is not limited to, nonwoven, fibrous sheet materials. In another and/or alternative aspect of this embodiment, the nonwoven material includes, but is not limited to, meltblown, coform, air-laid, spunbond, wet laid, bonded-carded web materials, and/or hydroentangled (also known as spunlaced) materials. In still another and/or alternative aspect of this embodiment, the woven material includes, but is not limited to, cotton fibers, cotton/nylon blends and/or other textiles. In another and/or alternative embodiment, the cleaning wipe includes a sponge and/or sponge-like material. In one aspect of this embodiment, the sponge and/or sponge-like material includes, but is not limited to, regenerated cellulose and/or polyurethane foams. In still another and/or alternative embodiment, the cleaning wipe includes, but is not limited to, wood pulp, a blend of wood pulp, and/or synthetic fibers. In one aspect of this embodiment, the synthetic fibers include, but are not limited to, polyester, rayon, nylon, polypropylene, polyethylene, and/or cellulose polymers. In still another and/or alternative embodiment, the cleaning wipe includes a binder.

The cleaning composition on the cleaning pad or cleaning wipe is typically in a ready to use liquid form; however, the cleaning composition can be in a concentrate in liquid, semi-liquid or solid form on the cleaning pad or cleaning wipe. Typically, the cleaning wipe has at least one layer of nonwoven material. The cleaning pad can also include one or more layers of nonwoven material.

Manufacturers of cleaning wipes that can be used in the present invention include, but are not limited to, Suominen, PGI, Kimberly-Clark, E.I. Du Pont de Nemours and Company, Dexter, American Nonwovens, and James River, BBA Nonwoven. Specific, nonlimiting examples of cleaning wipes from these manufacturers are disclosed in Bouchette et al., U.S. Pat. Nos. 4,781,974 and 4,615,937; Clark et al, U.S. Pat.

No. 4,666,621; Amundson et al., WO 98/03713; Cabell et al., U.S. Pat. No. 5,908,707; Mackey et al., WO 97/40814; Mackey et al., WO 96/14835; and Moore, EP 750063, all of which are incorporated herein by reference.

The cleaning pad typically has an absorbent capacity, when measured under a confining pressure of 0.09 psi after 20 minutes, of at least about 1 g deionized water per g of the cleaning pad. The cleaning pad will also typically have a total fluid capacity (of deionized water) of at least about 100 g. However, the absorbency and/or fluid capacity of the cleaning pad can vary depending on the desired use of the cleaning pad. The cleaning wipe can have the same or different amount of absorbency.

The loading ratio of the cleaning composition onto the cleaning wipe or cleaning pad can be about 2-5:1, and typically about 3-4:1; however, other loading ratios can be used. In a further and/or alternative embodiment, the liquid loading capacity of the cleaning wipe or pad is sufficient to retain the desired amount of cleaning composition on the cleaning wipe or pad. In one aspect of this embodiment, the liquid loading capacity of the cleaning wipe or pad is at least about 10% of the dry weight of the cleaning wipe or pad. In another and/or alternative aspect of this embodiment, the liquid loading capacity of the cleaning wipe or pad is about 50%-1000% of the dry weight of the cleaning wipe or pad. This loading capacity is expressed as loading ½ to 10 times the weight (or, more accurately, the mass) of the dry cleaning wipe or pad. In still another and/or alternative aspect of this embodiment, the liquid loading capacity of the cleaning wipe or pad is about 200%-800% of the dry weight of the cleaning wipe or pad. In yet another and/or alternative aspect of this embodiment, the liquid loading capacity of the cleaning wipe or pad is about 250%-500% of the dry weight of the cleaning wipe or pad. In still yet another and/or alternative aspect of this embodiment, the liquid loading capacity of the cleaning wipe or pad is about 300%-450% of the dry weight of the cleaning wipe or pad. In still a further and/or alternative embodiment, the cleaning composition is impregnated, dosed, loaded, metered, and/or otherwise dispensed onto the cleaning wipe or pad. The loading of the cleaning wipe or pad can be accomplished in several ways including, but not limited to, treating each individual wipe or pad with a discrete amount of cleaning composition, mass treating a continuous web of cleaning wipes with the cleaning composition, soaking the entire web of cleaning wipes in the cleaning composition, spraying the cleaning composition in a stationary or moving web of cleaning wipes, and/or impregnating a stack of individually cut and sized cleaning wipes or pad in a container and/or a dispenser. In another and/or alternative embodiment, the cleaning wipe or pad has a wet tensile strength of at least about 25-250 Newton/m. In one aspect of this embodiment, the cleaning wipe or pad has a wet tensile strength of about 25-250 Newton/m. In another and/or alternative aspect of this embodiment, the cleaning wipe or pad has a wet tensile strength of about 75-170 Newton/m. The cleaning composition can be loaded onto the cleaning wipe and/or cleaning pad in any number of manufacturing methods. Typically, the cleaning wipe or cleaning pad is sprayed with or soaked in the cleaning composition for a period of time until the desired amount of loading is achieved.

The cleaning pad or cleaning wipe can also be part of a cleaning kit or tool. The cleaning pad or cleaning wipe can also have an attachment layer that allows the cleaning pad or cleaning wipe to be connected to and/or disconnected from an implement's handle or the support head or an implement (e.g., mop, broom, etc.). The attachment layer can also function to prevent fluid flow through the top surface (e.g., the handle-contacting surface) of the cleaning pad or cleaning wipe, and/or can further provide enhanced integrity for the cleaning pad or cleaning wipe. The kit can have an assembly of one or more units, either packaged together or separately. The kit can comprise an implement containing a cleaning pad or cleaning wipe that may or may not include a superabsorbent material, and the cleaning composition. The cleaning pad or cleaning wipe can be detachably mounted on the implement so that the cleaning pad or cleaning wipe can be removed and/or replaced with a fresh clean pad or cleaning wipe. The implement can also have a reservoir that contains the cleaning composition. The reservoir can be refillable or contain a non-refillable amount of cleaning composition. The reservoir can also be detachably mounted on the implement to allow for easy refilling or replacing with a filled reservoir.

In still a further and/or alternative embodiment of the present invention, the cleaning wipes and/or pads can have an attachment layer that allows the wipe and/or pad to be connected to an implement's handle or the support head of various implements. The attachment layer is used in those embodiments where the absorbent and/or adsorbent layer is not suitable for attaching the wipe and/or pad to the support head of the handle. The attachment layer can also function as a mechanism to inhibit or prevent fluid flow through the top surface (e.g., the handle-contacting surface) of the cleaning wipe and/or pad, and/or can provide enhanced integrity of the wipe and/or pad. In one aspect of this embodiment, the attachment layer can consist of a mono-layer or a multi-layer structure. In another and/or alternative aspect of this embodiment, the attachment layer can comprise a surface which is capable of being mechanically attached to the handle's support head by use of a hook and loop system. In one specific design, the attachment layer can comprise at least one surface which is mechanically attachable to hooks that are affixed to the bottom surface of the handle's support head.

In another and/or alternative aspect of the present invention, the cleaning wipe or pad can be individually sealed with a heat-sealable and/or glueable thermoplastic overwrap such as, but not limited to, polyethylene, Mylar and the like. In one embodiment, the cleaning wipes or pads are packaged as numerous, individual sheets or pads which are at least partially, impregnated with the cleaning composition of the present invention. In another and/or alternative embodiment, the cleaning wipes are at least partially formed as a continuous web during the manufacturing process and loaded into a dispenser such as, but not limited to, a canister with a closure or a tub with closure. The closure is at least partially used to seal the loaded cleaning wipes from the external environment and/or prevent premature volatilization of the components of the cleaning composition. In one aspect of this embodiment, the dispenser includes a plastic such as, but not limited to, high density polyethylene, polypropylene, polycarbonate, polyethylene terephthalate (PET), polyvinyl chloride (PVC), and/or other rigid plastic. In another aspect and/or alternative of this embodiment, the continuous web of cleaning wipes is at least partially threaded through an opening in the top of the dispenser. In still another and/or alternative aspect of this embodiment, the dispenser includes a severing arrangement to cut at least a portion of the cleaning wipe after being at least partially removed from the dispenser. The severing arrangement can include, but is not limited to, a knife blade, serrated edge, and/or the like. In still yet another and/or alternative aspect of this embodiment, the continuous web of cleaning wipes can be scored, folded, segmented, and/or partially cut into uniform and/or non-uniform sizes, and/or lengths. In a further and/or alternative aspect of this embodiment, the cleaning wipes can be interleafed so that the removal of one cleaning wipe advances the next in the opening of the dispenser.

1. Experimental Procedure for Optical Microscopy of Droplet Residue

Figure 3:
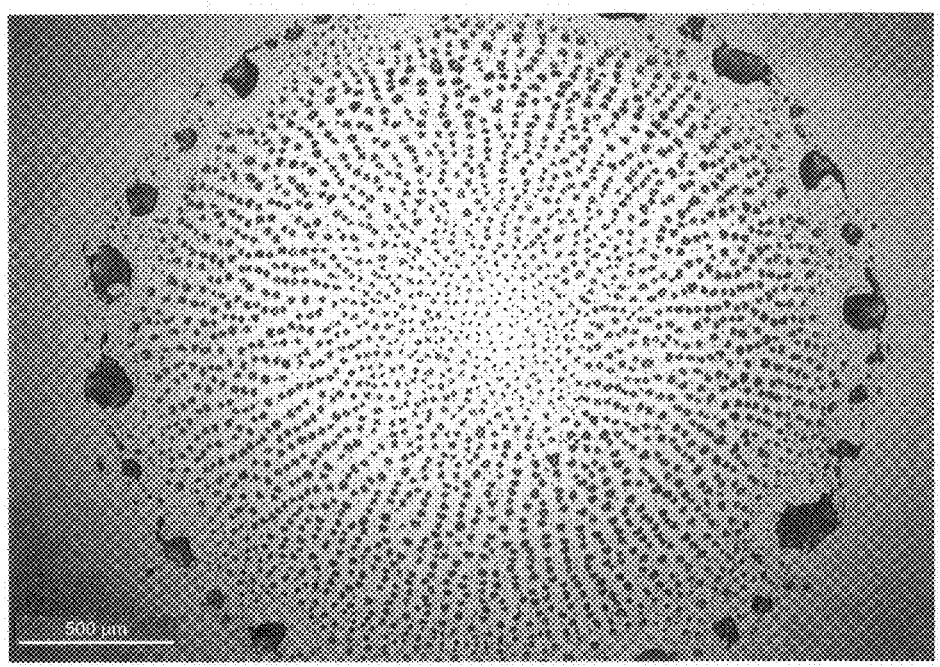
FIG. 3 is a microscopy image of a dried droplet residue of a cleaning composition according to the present invention with a low cloud point, 79° F., and a regular micron-structure.
Figure 4:
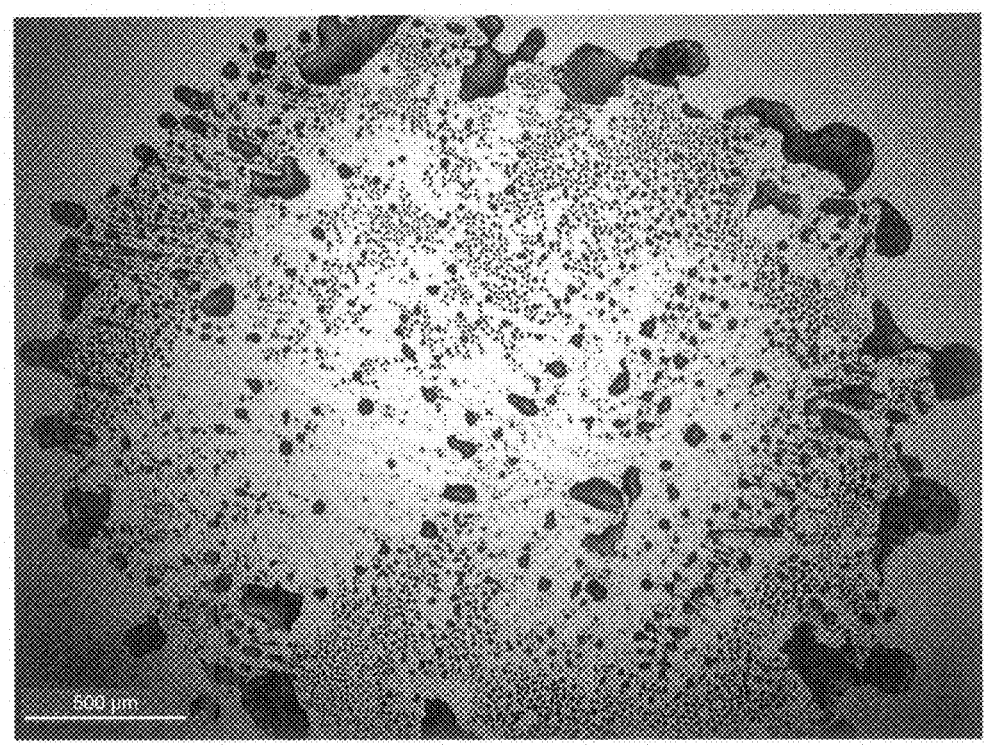
FIG. 4 is a microscopy image of a dried droplet residue of a cleaning composition with poor streaking and filming performance. The composition of the dried droplet has a high cloud point, 110° F., and an irregular micron-structure.
Figure 5:
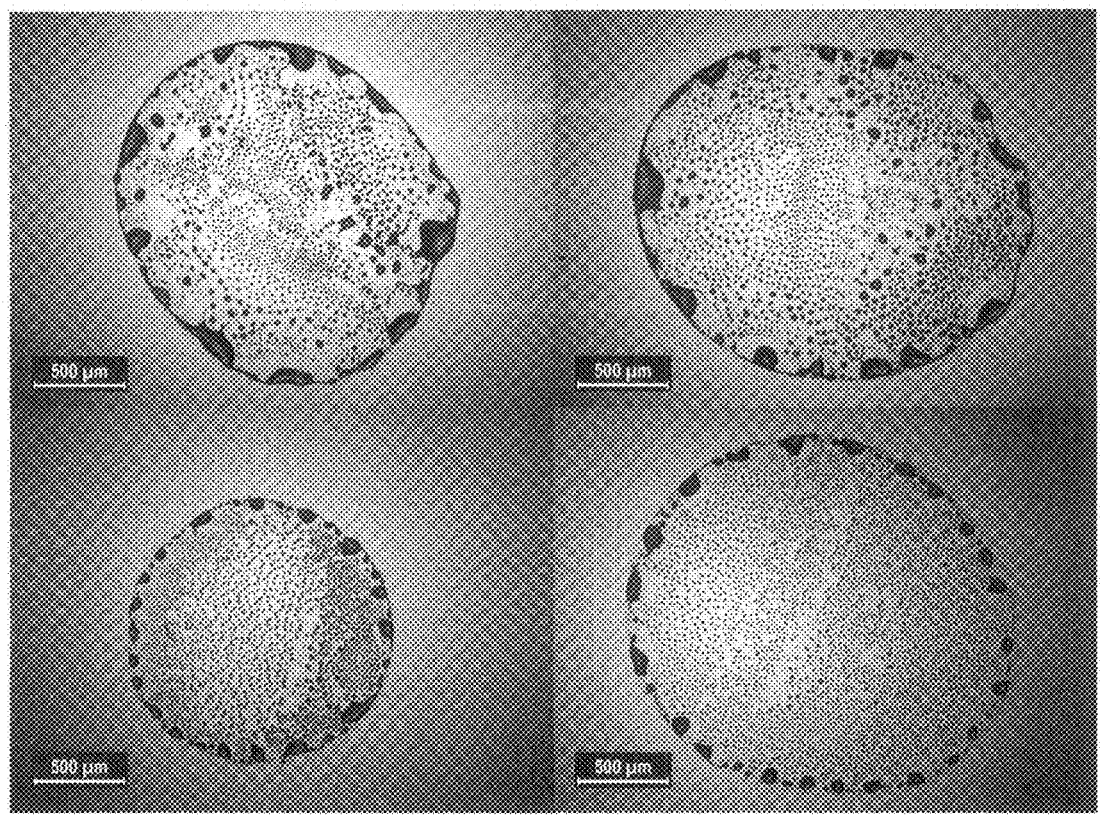
FIG. 5 is a set of four microscopy images showing the surface residue of a droplet of low-VOC cleaning compositions of the present invention with the same surfactant but different cloud points. The upper left composition has a cloud point of 85° F. The upper right composition has cloud point of 83° F. The lower left composition has a cloud point of 81° F. The lower right composition has a cloud point of 78° F.

FIGS. 3, 4 and 5 are all optical microscopy photos of droplet residues which were created using the following process.

Sample Preparation

Lotion samples were filtered through a 0.45 μm filter. 0.5 μl droplets of the lotion sample were placed on the clean polished surface of a silicon wafer (University Wafer, Part No. S3P01 SP) and left to dry at room temperature (23±2° C.), which generally took a few minutes. Multiple droplets for each sample were used to confirm the reproducibility of the experiment.

Microscopy

Dried droplets were imaged using a Leica DM2500 P microscope under the reflection mode. Images were digitally captured using a Leica DFC295 digital microscope color camera and Leica software Application Suite, LAS v3.6. In some cases real time movies of drying droplets were also captured using a LAS MultiTime-Movie-Timelapse module. All of the digital image analysis was performed using the NIH ImageJ 1.44p software.

Image Analysis

Images were converted to 8-bit and then to a binary format. Total number of micro-droplets (μ-droplets) on the image was counted under the 'Analyze Particles' subroutine of ImageJ software. Reported area of g-droplets was converted to an equivalent diameter by approximating the area to the area of a circle. A frequency histogram of μ-droplet sizes was then generated from this data. A mean diameter (d) and standard deviation (σ) was calculated for each distribution. A dispersity parameter was defined to be the ratio of standard deviation and mean (dispersity=σ/d).

FIG. 3 is a microscopy picture of a dried droplet residue of a cleaning composition according to the present invention with a low cloud point and a regular micron-structure. The formulation for the droplet residue shown in FIG. 3 is the one with the cloud point of 79° F. (shown in the table below). In contrast, FIG. 4 shows a microscopy picture of a dried droplet residue of a cleaning composition which does not meet the criteria of the present invention because it has an irregular residue structure and a high cloud point. The formulation for the droplet residue shown in FIG. 4 is the one with the cloud point of 110° F. (shown in the table below). Although, these formulations are very similar the droplet residue pictures in FIGS. 3 and 4 illustrate that without the proper amount of solvent, in this example it is hexyl cellosolve, the cloud point of the formulation may be too high and this results in a surface residue that is undesirable for hard surfaces. Conversely, FIG. 3 show a droplet residue with a relatively uniform micron-structure which appears substantially invisible to the human eye and is therefore desirable for hard surfaces. FIGS. 3 and 4 illustrate the importance of the right level of hexyl cellosolve in the composition (depending on the surfactant used) in a composition, the right cloud point temperature and the creation of a uniform droplet residue pattern.

Using the above described microscopy method, the uniformity of the droplet residue pattern can be measured by the following reproducible criteria: wherein when a 0.5 microliter drop of said composition deposited on a clean silicon surface, forms a circular residue where, within the central 80% of the droplet residue image, there is no position where a 200-micron diameter circle can be placed where it will contain no boundaries between the dark and light portions of the image. According to these criteria for the uniformity of the micron-structure in the droplet residue, FIG. 3 shows a droplet residue that meets the above uniformity criteria and FIG. 4 shows a droplet residue that does not meet the above uniformity criteria.

| | | | Weight % | |
|---|---|---|---|---|
| Ingredient | Purpose | Chemical Name | Cloud Point = 79° F. | Cloud Point = 110° F. |
| Water | Water | | 95.73 | 96.67 |
| Sodium Bicarbonate | Buffer | | 0.0006 | 0.0006 |
| Citric Acid | Buffer | | 0.0005 | 0.0005 |
| BTC 2125M-NA | Active | 1. n-Alkyl (C14 60%; c16 30%; C12 5%; C16 5%) dimethyl benzyl ammonium chloride (50%). 2. n-Alkyl (C12 68%; C14 32%) dimethyl ethylbenzyl ammonium chloride (50%). | 0.73 | 0.73 |
| Isopropyl alcohol | Solvent | | 0.45 | 0.45 |
| Surfonic P3 Surfactant | Surfactant | A straight-chain primary aliphatic alkoxylated alcohol | 0.44 | 0.44 |
| Hexyl Cellosolve | Solvent | Ethylene Glycol Monohexyl Ether | 2.468 | 1.527 |
| Fragrance | Fragrance | | 0.18 | 0.18 |

FIG. 5 contains a set of four microscopy images created according to the procedure outlined above. FIG. 5 showing the surface residue of a droplet of low-VOC cleaning compositions of the present invention with the same surfactant, but different cloud points. The level of hexyl cellosolve in the cleaning compositions was varied to create samples with different cloud points. The upper left composition has a cloud point of 85° F. The upper right composition has cloud point of 83° F. The lower left composition has a cloud point of 81° F. The lower right composition has a cloud point of 78° F. It is clear based on these residue photos that the regularity/uniformity of the micron-structure starts to break down and become less regular around 85° F. The level of the glycol ether solvent was varied to achieve samples at these cloud point temperatures. This exemplary cleaning composition used to create these droplet residues has the following general formulation.

FIG. 5 Formulation

| | |
|---|---|
| Quaternary Amine | 0.01-1% |
| Glycol Ether Solvent | 0.5-3% |
| Alcohol Solvent | 0.1-2% |
| EO-PO Surfactant | 0.001-1% |
| Buffer | 0.001-1% |
| Fragrance | 0.001-1% |
| Water | 90-99% |

Figure 2:
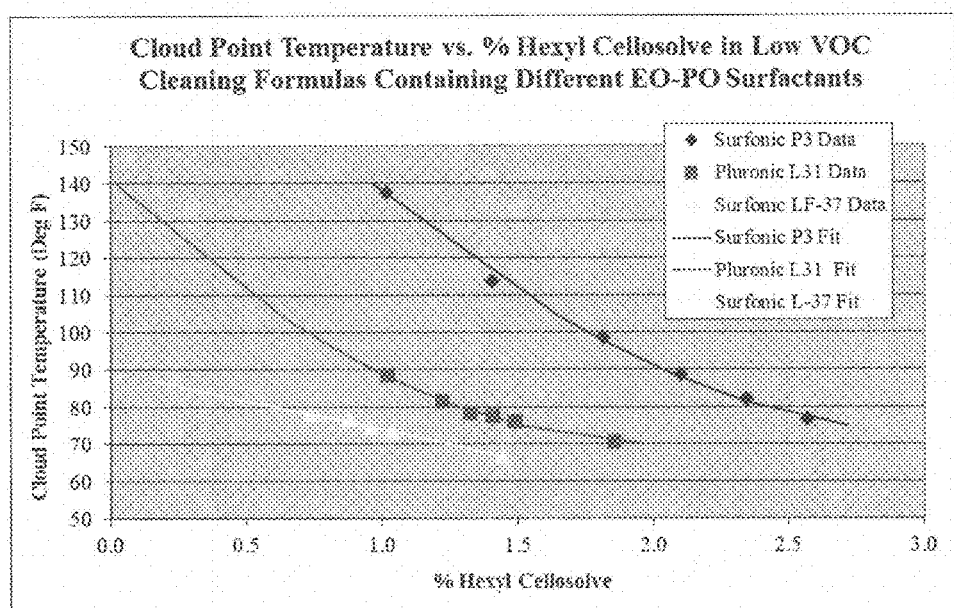
FIG. 2 is a graph showing how three EO-PO surfactants have varying cloud points depending on the weight % of ethylene glycol monohexyl ether in the composition.

FIGS. 1 and 2 further illustrate how different cleaning compositions with different types of nonionic surfactants require varying amounts of hexyl cellosolve solvent to achieve the same could point temperatures. Although the amount of hexyl cellosolve required to reach a particular cloud point may vary depending on the surfactant, the addition of the appropriate amount of hexyl cellosolve can be used to achieve a low cloud point cleaning composition with a regular residue microstructure which creates the appearance of low streaking and filming on hard surfaces.

A general formulation of the low-VOC cleaning composition in weight percent for hard surface cleaning is as follows:

| | |
|---|---|
| Cationic Biocide | 0.01-2% |
| Surfactant | 0.01-2% |
| VOC solvent | less than about 5% |
| Water | less than about 99.95% |

Several specific, nonlimiting, examples of the low VOC cleaning composition according to the present invention in weight percent are shown in Table I.

TABLE I

| Formulation Components % by wt. | Surfonic LF-41 Formulation | Surfonic P3 Formulation | Surfonic LF-18 Formulation | Pluronic L31 Formulation | Pluronic L35 Formulation | Surfonic LF-37 Formulation |
|---|---|---|---|---|---|---|
| % Water | 96.32 | 96.09 | 97.07 | 97.23 | 96.50 | 97.88 |
| % Quat | 0.37 | 0.37 | 0.37 | 0.37 | 0.37 | 0.37 |
| % IPA | 0.45 | 0.45 | 0.45 | 0.45 | 0.45 | 0.45 |
| % Surfactant | 0.44 | 0.44 | 0.44 | 0.44 | 0.44 | 0.44 |
| % Fragrance | 0.18 | 0.18 | 0.18 | 0.18 | 0.18 | 0.18 |
| % Low VOC Solvent (i.e. Ethylene Glycol Monohexyl Ether) | 2.24 | 2.47 | 1.49 | 1.33 | 2.06 | 0.68 |
| Cloud Point Temp (° F.) | 79 | 79 | 79 | 79 | 79 | 79 |

In contrast to Table I, several specific, nonlimiting, examples of the low VOC cleaning compositions that have high cloud points and exhibit undesirable streaking and filming residues are shown below in Table II. The formulation components are in weight percent in Table II.

TABLE II

| Formulation Components % by wt. | Surfonic LF-41 Formulation | Surfonic P3 Formulation | Surfonic LF-18 Formulation | Pluronic L31 Formulation | Pluronic L35 Formulation | Surfonic LF-37 Formulation |
|---|---|---|---|---|---|---|
| % Water | 97.41 | 97.03 | 98.23 | 98.04 | 96.96 | 98.56 |
| % Quat | 0.37 | 0.37 | 0.37 | 0.37 | 0.37 | 0.37 |
| % IPA | 0.45 | 0.45 | 0.45 | 0.45 | 0.45 | 0.45 |
| % Surfactant | 0.44 | 0.44 | 0.44 | 0.44 | 0.44 | 0.44 |
| % Fragrance | 0.18 | 0.18 | 0.18 | 0.18 | 0.18 | 0.18 |
| % Low VOC Solvent (i.e. Ethylene Glycol Monohexyl Ether) | 1.15 | 1.53 | 0.33 | 0.52 | 1.60 | 0.00 |
| Cloud Point Temp (° F.) | 110 | 110 | 110 | 110 | 110 | 110 |

Table I shows a number of exemplary formulations of the present invention containing different EO-PO surfactants which show that very similar formulations with different surfactants require varying levels of hexyl cellosolve solvent to achieve the same cloud point level. If the goal is to create formulations with a low cloud point, then the amount of hexyl cellosolve required for each formulation will vary depending on the specific surfactant chosen for the formulation. Depending on the specific formulation, a low cloud point of less than about 95° F., or less than about 90° F. or even less than about 85° F., will be sufficient to create a cleaning composition with low streaking and filming, characterized by a droplet residue with a regular micron-structure. What is consistent with all the formulations in Table I is that they all have a low cloud point and they all exhibit a uniform micron-structure upon drying on a treated surface. In contrast, Table II shows formulations that are relatively similar to those in Table I, but for each type of surfactant composition the level of hexyl cellosolve has gone down, relative to the level in Table I for the same surfactant composition, and the cloud point is high, 110° F. What is consistent about each of the formulations in Table II is that they do not meet the criteria of the claimed present invention because they all exhibit irregular residue films upon drying on a surface and they all have a high cloud point. Most low-VOC formulations with a cloud point over 95° F. do not exhibit good streaking and filming performance and therefore they are undesirable cleaning compositions for hard surfaces.

The following formulations are non-limiting examples of formulations according to the present invention.

Example 1

| | |
|---|---|
| Cationic Biocide | 0.01-2% |
| VOC Solvent | 0.01-4% |
| Surfactant | 0.001-1% |
| Buffer | 0.001-1% |
| Fragrance | 0.001-1% |
| Biocide release agent | 0-10% |
| Water | 0-99.95% |

Example 2

| | |
|---|---|
| Cationic Biocide | 0.01-1% |
| VOC Solvent | 0.01-2% |
| Surfactant | 0.001-1% |
| Buffer | 0.001-1% |
| Fragrance | 0.001-1% |
| Biocide release agent | 0-10% |
| Water | 90-99.95% |

Example 3

| | |
|---|---|
| Cationic Biocide | 0.01-1% |
| VOC Solvent | 0.01-2% |
| EO-PO Surfactant | 0.001-1% |
| Buffer | 0.001-1% |
| Fragrance | 0.001-1% |
| Biocide release agent | 0-3% |
| Water | 90-99.95% |

Example 4

| | |
|---|---|
| Cationic Biocide | 0.01-1% |
| Alcohol | 0.01-2% |
| Low-VOC Solvent | 0.01-3% |
| Surfactant | 0.001-1% |
| Buffer | 0.001-1% |
| Fragrance | 0.001-1% |
| Biocide release agent | 0-3% |
| Water | 90-99.95% |

Example 5

| | |
|---|---|
| Cationic Biocide | 0.05-5% |
| Glycol Ether Solvent | 0.05-10% |
| Nonionic Surfactant | 0.01-5% |
| Buffer | 0-2% |
| Fragrance | 0-1% |
| Biocide release agent | 0-3% |
| Water | at least 80% |

Example 6

| | |
|---|---|
| Cationic Biocide | 0.05-5% |
| First Solvent | 0.05-10% |
| Second Solvent | 0-2% |
| Nonionic Surfactant | 0.01-5% |
| Buffer | 0-2% |
| Fragrance | 0-1% |
| Biocide release agent | 0-3% |
| Water | at least 90% |

Example 7

| | |
|---|---|
| Cationic Biocide | 0.05-5% |
| Glycol Ether Solvent | 0.05-10% |
| Second Solvent | 0-2% |
| Nonionic Surfactant | 0.01-5% |
| Buffer | 0-2% |
| Fragrance | 0-1% |
| Biocide release agent | 0-3% |
| Water | at least 80% |

Example 8

| | |
|---|---|
| Cationic Biocide | 0.05-2% |
| Glycol Ether Solvent | 0.05-10% |
| Second Solvent | 0-2% |
| EO-PO Surfactant | 0.01-5% |
| Buffer | 0-2% |
| Fragrance | 0-1% |
| Water | at least 90% |

The invention has been described with reference to a preferred embodiment and alternates thereof. It is believed that many modifications and alterations to the embodiments disclosed will readily suggest themselves to those skilled in the art upon reading and understanding the detailed description of the invention. It is intended to include all such modifications and alterations insofar as they come within the scope of the present invention.

We claim:

1. A cleaning substrate comprising:
   a. a substrate;
   b. a cleaning composition, loaded onto said substrate, consisting of:
      i. about 0.05-5% by weight of one or more cationic biocide,
      ii. about 0.01-5% by weight of one or more surfactant,
      iii. about 0.05-5% by weight of a first solvent comprising a glycol ether,
      iv. about 0.01-2% by weight of a second solvent selected form the group consisting of: alcohols, diols, C1-10 alkyl ethers of alkylene glycols, C3-24 alkylene glycol ethers; polyalkylene glycols, short chain carboxylic acids, short chain esters, isoparaffinic hydrocarbons, mineral spirits, alkylaromatics, terpenes, terpene derivatives, terpenoids, terpenoid derivatives, formaldehyde, pyrrolidones, water, and any mixtures or combinations thereof; and
      v. optionally, one or more adjuncts selected from the group consisting of: buffers, fragrances, perfumes, builders, stabilizers, defoamers, thickeners, hydrotropes, biocide release agents, anti-microbial compounds, enzymes, bleaching agents, cloud point modifiers, and preservatives.

2. The cleaning substrate as defined in claim 1, wherein the composition further comprises a buffer.

3. The cleaning substrate as defined in claim 1, wherein the composition further comprises a fragrance.

4. The cleaning substrate as defined in claim 1, wherein said second solvent comprises an alcohol.

5. The cleaning substrate as defined in claim 1, wherein said alkoxylate surfactant is selected from the group consisting of: ethoxylate surfactants, propoxylate surfactants, ethoxylate-propoxylate copolymer surfactants and any mixtures or combinations thereof.

6. The cleaning substrate as defined in claim 1, wherein said surfactant comprises a non-ionic surfactant.

7. The cleaning substrate as defined in claim 1, wherein said cationic biocide includes a quaternary ammonium compound.

8. The cleaning substrate as defined in claim 1, wherein said surfactant is selected from the group consisting of: ethylene oxide and propylene oxide alcohols, ethylene oxide and mixed ethylene oxide/propylene oxide adducts of alkylphenols, the ethylene oxide and mixed ethylene oxide/propylene oxide adducts of fatty acids, mixed ethylene oxide/propylene oxide block copolymers, and any mixtures or combinations thereof.

9. A cleaning substrate comprising:
   a. a substrate;
   b. a cleaning composition, loaded onto said substrate, consisting of:
      i. about 0.05-5% by weight of one or more quaternary ammonium compound,
      ii. about 0.01-5% by weight of one or more non-ionic surfactant, and
      iii. about 0.05-5% by weight of a first solvent comprising a glycol ether,
      iv. about 0.01-2% by weight of a second solvent selected form the group consisting of: alcohols, diols, C1-10 alkyl ethers of alkylene glycols, C3-24 alkylene glycol ethers; polyalkylene glycols, short chain carboxylic acids, short chain esters, isoparaffinic hydrocarbons, mineral spirits, alkylaromatics, terpenes, terpene derivatives, terpenoids, terpenoid derivatives, formaldehyde, pyrrolidones, water, and any mixtures or combinations thereof; and
      v. optionally, one or more adjuncts selected from the group consisting of: fragrances, perfumes, buffers, builders, stabilizers, defoamers, thickeners, hydrotropes, biocide release agents, water, anti-microbial compounds, enzymes, bleaching agents, cloud point modifiers, non-ionic surfactants and preservatives.

10. The cleaning substrate as defined in claim 9, wherein the composition further comprises a buffer.

11. The cleaning substrate as defined in claim 9, wherein said substrate comprises a fibrous non-woven material.

12. The cleaning substrate as defined in claim 9, wherein said substrate comprises at least two or more layers of non-woven materials.

13. The cleaning substrate as defined in claim 9, wherein said non-ionic surfactant is selected from the group consisting of: ethoxylate surfactants, propoxylate surfactants, ethoxylate-propoxylate copolymer surfactants and any mixtures of combinations thereof.

14. The cleaning composition as defined in claim 9, wherein said second solvent comprises an alcohol.

15. A cleaning composition consisting of:
   i. about 0.05-5% by weight of one or more cationic biocide,
   ii. about 0.01-5% by weight of one or more non-ionic surfactant,
   iii. about 0.05-5% by weight of a first solvent comprising a glycol ether,
   iv. about 0.01-2% by weight of a second solvent selected form the group consisting of: alcohols, diols, C1-10 alkyl ethers of alkylene glycols, C3-24 alkylene glycol ethers; polyalkylene glycols, short chain carboxylic acids, short chain esters, isoparaffinic hydrocarbons, mineral spirits, alkylaromatics, terpenes, terpene derivatives, terpenoids, terpenoid derivatives, formaldehyde, pyrrolidones, water, and any mixtures or combinations thereof;
   v. one or more buffering agent; and
   vi. optionally, one or more adjuncts selected from the group consisting of: fragrances, perfumes, builders, stabilizers, defoamers, thickeners, hydrotropes, biocide release agents, anti-microbial compounds, enzymes, bleaching agents, cloud point modifiers, and preservatives.

16. The cleaning composition as defined in claim 15, wherein said cationic biocide includes a quaternary ammonium compound.

17. The cleaning composition as defined in claim 15, wherein said non-ionic surfactant is selected from the group consisting of: ethylene oxide and propylene oxide alcohols, ethylene oxide and mixed ethylene oxide/propylene oxide adducts of alkylphenols, the ethylene oxide and mixed ethylene oxide/propylene oxide adducts of fatty acids, mixed ethylene oxide/propylene oxide block copolymers, and any mixtures or combinations thereof.

18. The cleaning composition as defined in claim 15, wherein said non-ionic surfactant is an alkoxylate surfactant.

19. The cleaning composition as defined in claim 18, wherein said alkoxylate surfactant is selected from the group consisting of: ethoxylate surfactants, propoxylate surfactants, ethoxylate-propoxylate copolymer surfactants and any mixtures or combinations thereof.

20. The cleaning composition as defined in claim 15, wherein said cationic biocide includes a quaternary ammonium compound.

* * * * *